United States Patent
Kawa et al.

(10) Patent No.: US 8,921,430 B2
(45) Date of Patent: Dec. 30, 2014

(54) ESTER MIXTURES AND COMPOSITIONS COMPRISING SUCH ESTER MIXTURES

(75) Inventors: Rolf Kawa, Monheim (DE); Stefan Brüning, Düsseldorf (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 13/380,622

(22) PCT Filed: Jun. 19, 2010

(86) PCT No.: PCT/EP2010/003712
§ 371 (c)(1),
(2), (4) Date: Dec. 23, 2011

(87) PCT Pub. No.: WO2011/000488
PCT Pub. Date: Jan. 6, 2011

(65) Prior Publication Data
US 2012/0095115 A1    Apr. 19, 2012

(30) Foreign Application Priority Data

Jun. 30, 2009  (EP) ..................................... 09008543
Aug. 8, 2009   (EP) ..................................... 09010269

(51) Int. Cl.
| | | |
|---|---|---|
| A61K 47/00 | (2006.01) | |
| A01N 25/00 | (2006.01) | |
| A61Q 19/00 | (2006.01) | |
| A61K 8/37 | (2006.01) | |
| A61Q 1/02 | (2006.01) | |
| A61Q 1/06 | (2006.01) | |
| A61Q 5/12 | (2006.01) | |
| A61Q 17/04 | (2006.01) | |

(52) U.S. Cl.
CPC . *A61Q 19/00* (2013.01); *A61K 8/37* (2013.01); *A61Q 1/02* (2013.01); *A61Q 1/06* (2013.01); *A61Q 5/12* (2013.01); *A61Q 17/04* (2013.01)
USPC .......................................... 514/785; 514/784

(58) Field of Classification Search
None
See application file for complete search history.

(56) References Cited

U.S. PATENT DOCUMENTS

| | | | |
|---|---|---|---|
| 5,609,854 A | 3/1997 | Guerrero et al. | |
| 5,705,169 A | 1/1998 | Stein et al. | |
| 5,840,943 A | 11/1998 | Ansmann et al. | |
| 5,945,091 A | 8/1999 | Habeck et al. | |
| 6,793,929 B2 | 9/2004 | Bleckmann et al. | |
| 2009/0182046 A1* | 7/2009 | Dierker et al. ................ | 514/547 |
| 2009/0202461 A1 | 8/2009 | Rodriguez et al. | |

FOREIGN PATENT DOCUMENTS

| | | |
|---|---|---|
| DE | 1972033 | 9/1998 |
| DE | 10340412 | 4/2005 |
| EP | 0271139 | 6/1988 |
| EP | 0766661 B1 | 4/1997 |
| EP | 0694521 | 1/1998 |
| EP | 0923935 | 6/1999 |
| EP | 1055424 | 11/2000 |
| EP | 2147954 | 1/2010 |
| FR | 2871689 | 12/2005 |
| JP | S63-154640 | 6/1988 |
| JP | H01-294650 | 11/1989 |
| JP | H03-008110 | 1/1991 |
| JP | H08-333219 | 12/1996 |
| JP | H09-227383 | 9/1997 |
| JP | H10-237759 | 9/1998 |
| JP | H11-071249 | 3/1999 |
| JP | H11-310741 | 11/1999 |
| JP | 2002-532581 | 10/2002 |
| JP | 2003-137758 | 5/2003 |
| JP | 2003-238484 | 8/2003 |
| JP | 2003-300930 | 10/2003 |
| JP | 2006-020526 | 1/2006 |
| JP | 2006-028180 | 2/2006 |
| JP | 2006-282662 | 10/2006 |
| JP | 2007-509025 | 4/2007 |
| JP | 2008-509288 | 3/2008 |
| JP | 2008-542425 | 11/2008 |
| JP | 2010-100590 | 5/2010 |
| WO | WO-95/00107 | 1/1995 |
| WO | WO-99/06021 | 2/1999 |
| WO | WO-00/35968 | 6/2000 |

(Continued)

OTHER PUBLICATIONS

"Captylic/capric acid ester of saturated fatty alcohol C12-18", *Cogis Product Data Sheet*, XP-002547755, Rev. No. 3-06 2004, 3 pgs.

(Continued)

*Primary Examiner* — Ernst V Arnold
*Assistant Examiner* — Kyung Sook Chang
(74) *Attorney, Agent, or Firm* — Servilla Whitney LLC

(57) ABSTRACT

The invention is directed to a mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms, wherein the mixture comprises 5 to 60 weight-% of ester of the general formula (I), wherein $R_1$ is an alkyl moiety with 9 carbon atoms, based on the total amount of esters according to formula (I) and/or wherein the mixture comprises 5 to 60 weight-% of ester of the general formula (I), wherein $R_2$ is an alkyl moiety with 10 carbon atoms, based on the total amount of esters according to formula (I). The invention is further directed to cosmetic and/or pharmaceutical compositions comprising such esters and processes for the production of such esters.

19 Claims, No Drawings

(56) References Cited

FOREIGN PATENT DOCUMENTS

| WO | WO 0117492 A1 * | 3/2001 |
| WO | WO-2005/042681 | 5/2005 |
| WO | WO-2006/010087 | 1/2006 |
| WO | WO-2006/097235 | 9/2006 |
| WO | WO-2008/130040 | 10/2008 |

OTHER PUBLICATIONS

"Commission Directive 2005/9/EC", *Official Journal of the European Union* Jan. 29, 2005, 2 pgs.

PCT International Search Report in PCT/EP2010/003712, mailed Aug. 4, 2010, 3 pgs.

PCT IPRP in PCT/EP2010/003712, issued Jan. 2, 2012, 10 pgs.

Finkel, P., "Formulierung kosmetischer Sonnenschutzmittel", *Parf. Kosm. 80* 1999, 10-16.

Finkel, P., "Formulierung kosmetischer Sonnenschutzmittel", *Lichtschutz SOFW—Journal*, 122 1996, 543-548.

Griffin, William C., "Calculation of HLB Values of Non-Ionic Surfactants", *Journal of the Society of Cosmetic Chemists* 1954, 249-256.

Griffin, William C., "Classification of Surface-Active Agents by "HLB"", *Journal of the Society of Cosmetic Chemists* 1949, 311-326.

Kirk-Othmer "Encyclopedia of Chemical Technology, Third Edition, vol. 8", *John Wiley & Sons* 1979, 5 pgs.

* cited by examiner

1

ESTER MIXTURES AND COMPOSITIONS COMPRISING SUCH ESTER MIXTURES

CROSS REFERENCE TO RELATED APPLICATIONS

This application is a National Stage Entry of International Application No. PCT/EP2010/003712, filed Jun. 19, 2010, which claims priority to European Patent Application No. 09008543, filed June 30, 2009, and European Patent Application No. 09010269, filed Aug. 8, 2009, each of which is incorporated herein by reference in its entirety.

FIELD OF THE INVENTION

This invention relates to ester mixtures and to cosmetic and/or pharmaceutical compositions comprising such ester mixtures.

BACKGROUND OF THE INVENTION

Cosmetic hair and skin-care emulsions are expected by the consumer to satisfy a number of requirements. Apart from the cleansing and caring effects which determine the particular application, importance is attributed to such diverse parameters as highest possible dermatological compatibility, good lipid-layer-enhancing properties, elegant appearance, optimal sensory impression and shelf life.

Besides a number of surfactants, cosmetic hair- and skin-care preparations generally contain, above all, oil components and water. The oil component (emollients) used include, for example, hydrocarbons, ester oils and vegetable and animal oils/fats/waxes. In order to satisfy stringent market requirements in regard to sensory properties and optimal dermatological compatibility, new oil components and emulsifier mixtures are being continuously developed and tested. The use of ester oils in cosmetic products has been known for some time. Volatile silicone oils (cyclopentasiloxane, cyclohexasiloxane) are synthetic substances which evaporate on skin and provide specific properties such as high spreading, anti-tackiness and non greasy skin feel. The use of volatile silicones is widely spread but has been recently under review due to their possible negative effect towards the environment (bioaccumulation) and health. A drawback of known ester oils is their dissatisfactory sensory performance in comparison to silicon oils. One of the goals of the present invention was to provide substances, which can be used as (at least partial) replacement for silicon oils, which provide sensory properties which are comparable to known silicon oils. It was also desirable to provide substances which display better biodegradability and/or less irritation potential, e.g. better skin and/or eye tolerance. One of the goals of the present invention was to provide substances, which can be used as (at least partial) replacement for silicon oils, but which at the same time do not display a whitening effect: the so-called whitening effect is perceived to be due to foaming of emulsions and results in a whitish look of a composition when it is applied to the skin. One of the aims of the present invention was to provide substances, which reduce or diminish the whitening effect in cosmetic and/or pharmaceutical compositions.

SUMMARY OF THE INVENTION

The problem addressed by the present invention was to provide esters, which are preferably liquid at 20° C. for cosmetic applications which would have an improved profile in regard to their sensory properties (lightness, non-greasy skin feel, softness, smoothness, spreadability, absorption, distribution behavior, oiliness) and which can be incorporated in a number of cosmetic formulations. Such esters should also be able to serve as a basis for pharmaceutical compositions. The hydrolysis stability of the esters and their capacity for formulation at low pH values would also be of interest in this regard. Furthermore, especially for make-up formulations, the non transfer property is of enhanced interest. In addition the compatibility of the esters with detergent containing compositions (e.g. in shower gel, shampoo, hair conditioner) was of interest.

In addition, the esters should be easily incorporated in both w/o and in o/w formulations and water system like body oil, lipstick lipgloss and the like as well AP/Deo sticks and should be compatible in particular with crystalline UV filters, pigments, antiperspirants, salts and silicones and silicone derivatives. It has surprisingly been found that ester mixtures as described herein lead to sensorically light products. It has surprisingly been found that the ester mixtures as described herein reduce the whitening effect in cosmetic and/or pharmaceutical compositions.

Cetiol® LC is an ester mixture commercially available from Cognis GmbH, which is obtained by esterification of a C8 to C10 fatty acid with a saturated fatty alcohol C12 to C18. This ester mixture does not comprise esters according to formula (I), wherein $R_2$ is an alkyl moiety 8 to 10 carbon atoms. Unfortunately, these esters are problematic in solubilizing crystalline UV filters as well as solubilizing powders or pigment wetting agents. Surprisingly it has been found that the ester mixtures according to the invention displays an improved solubilizing capacity for these agents in comparison to the ester mixture Cetiol® LC. It has furthermore been found, that the ester mixture according to the invention display a higher spreading value in comparison to Cetiol® LC. Accordingly, the problem addressed by the present invention was to provide ester mixtures that would be improved in relation to the prior art, more particularly ester mixtures which could readily be formulated together with UV filters and, at the same time, would not have any disadvantages compared to the prior art in regard to sensory impression (so called "skin feel" or "skin afterfeel").

DETAILED DESCRIPTION OF THE INVENTION

The present invention relates to mixture of esters according to the general formula (I),

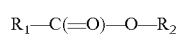

wherein $R_1$ is an alkyl moiety with 7 to 9 carbon atoms and wherein $R_2$ is a an alkyl moiety with 8 to 10 carbon atoms, wherein the mixture comprises 5 to 60 weight-% of ester of the general formula (I), wherein $R_1$ is an alkyl moiety with 9 carbon atoms, based on the total amount of esters according to formula (I) and/or wherein the mixture comprises 5 to 60 weight-% of ester of the general formula (I), wherein $R_2$ is an alkyl moiety with 10 carbon atoms, based on the total amount of esters according to formula (I). The ester mixture according to the invention comprises at least two different esters according to formula (I).

Surprisingly, the ester mixtures (synonymously used are the term "esters" and "mixture of esters") according to the invention are particularly suitable for cosmetic and/or pharmaceutical compositions, more particularly for compositions expected to impart a "light" skin feel. They display a sensory profile which is comparable to volatile silicones such as cyclomethicone. The esters can be incorporated particularly well in various formulations. Liquid substance mixtures are obtained and may be preferably used as oil components or consistency factors. Surprisingly, the ester mixtures according to the invention are particularly suitable for solubilising crystalline UV filters as well improving the ability of a powder to be dispersed (so called powder or pigment wetting or dispersing agent). The esters according to the invention are therefore especially suitable as solubilising agents or wetting agents in cosmetic and/or pharmaceutical compositions.

One embodiment of the invention is directed to a mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms, wherein the mixture comprises 5 to 60 weight-% of ester of the general formula (I), wherein $R_1$ is an alkyl moiety with 9 carbon atoms, based on the total amount of esters according to formula (I).

One embodiment of the invention is directed to a mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms, wherein the mixture comprises 5 to 60 weight-% of ester of the general formula (I), wherein $R_2$ is an alkyl moiety with 10 carbon atoms, based on the total amount of esters according to formula (I).

One embodiment of the invention relates to mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms, wherein the mixture comprises 5 to 60 weight-% of ester of the general formula (I), wherein $R_1$ is an alkyl moiety with 9 carbon atoms, based on the total amount of esters according to formula (I), and wherein the mixture comprises 5 to 60 weight-% of ester of the general formula (I), wherein $R_2$ is an alkyl moiety with 10 carbon atoms, based on the total amount of esters according to formula (I).

An embodiment of the invention is directed to ester mixtures according to the general formula (I), wherein the mixture comprises 5 to 40, preferably 5 to 20 weight-%, more preferably 5 to 10 weight-% of ester of the general formula (I), wherein $R_1$ is an alkyl moiety with 9 carbon atoms, based on the total amount of esters according to formula (I). An embodiment of the invention is directed to ester mixtures according to the general formula (I), wherein the mixture comprises 20 to 40 weight-% of ester of the general formula (I), wherein $R_1$ is an alkyl moiety with 9 carbon atoms, based on the total amount of esters according to formula (I). An embodiment of the invention is directed to ester mixtures according to the general formula (I), wherein the mixture comprises 40 to 60 weight-% of ester of the general formula (I), wherein $R_1$ is an alkyl moiety with 9 carbon atoms, based on the total amount of esters according to formula (I).

An embodiment of the invention is directed to a mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms, wherein the mixture comprises 5 to 40 weight-%, preferably 5 to 20 weight-%, more preferably 5 to 10 weight-% of ester of the general formula (I), wherein $R_2$ is an alkyl moiety with 10 carbon atoms, based on the total amount of esters according to formula (I). An embodiment of the invention is directed to a mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms, wherein the mixture comprises 20 to 40 weight-%, of ester of the general formula (I), wherein $R_2$ is an alkyl moiety with 10 carbon atoms, based on the total amount of esters according to formula (I). An embodiment of the invention is directed to a mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms, wherein the mixture comprises 40 to 60 weight-%, of ester of the general formula (I), wherein $R_2$ is an alkyl moiety with 10 carbon atoms, based on the total amount of esters according to formula (I).

In formula (I) $R_1$ is an alkyl moiety with 7 to 9 carbon atoms. Suitable alkyl moieties $R_1$ are linear or branched, saturated or unsaturated alkyl moieties. Examples of suitable alkyl moieties $R_1$ are n-heptyl, 1-methylhexyl-, 2-methylhexyl-, 3-methylhexyl-, 4-methylhexyl-, 5-methylhexyl, 1-ethyl-pentyl 1-hepentyl, 2-heptenyl, 3-heptenyl-, 4-heptenyl-, 5-heptenyl, 6-heptenyl-, n-octyl, 2-Ethylhexyl-, 1,1,3,3-Tetramethylbutyl, n-nonyl-, iso-nonyl (preferably 3,5,5 trimethylhexyl-, 2,4,4, trimethylpentyl-) moieties. In a preferred embodiment of the invention, $R_1$ is a linear alkyl moiety. In a preferred embodiment of the invention $R_1$ is a saturated alkyl moiety. Examples of suitable linear and saturated alkyl moieties $R_1$ are n-heptyl, n-octyl-, and n-nonyl.

In formula (I) $R_2$ is an alkyl moiety with 8 to 10 carbon atoms. Suitable alkyl moieties $R_2$ are linear or branched, saturated or unsaturated alkyl moieties. Examples of suitable alkyl moieties $R_2$ are n-octyl, 2-ethylhexyl-, 1,1,3,3-tetramethylbutyl, n-nonyl-, n-decyl-, 2-propyl-heptyl, 3-propyl-heptyl, 4-propyl-heptyl, iso-nonyl (preferably 3,5,5 trimethylhexyl or 2,4,4-trimethyl), iso-decyl (preferably 3,5-dimethyl-octyl, trimethyl-heptyl) moieties. In a preferred embodiment of the invention, $R_2$ is a linear alkyl moiety. In a preferred embodiment of the invention $R_2$ is a saturated alkyl moiety.

A preferred embodiment of the invention is directed to an ester mixture according to formula (I), wherein the amount of branched esters is 50 or less than 50 weight-%, preferably 40 or less than 40 weight-%, is 30 or less than 30 weight-%, is 25 or less than 25 weight-%, is 20 or less than 20 weight-%, is 15 or less than 15 weight-%, is 10 or less than 10 weight-%, preferably 5 or less than 5 weight-%, most preferably 1 or less than 1 weight.-%, based on the total amount of esters according to formula (I). A branched ester according to the invention is an ester according to formula (I) wherein $R_1$ and/or $R_2$ carry a branched alkyl moiety.

Preferably the ester mixture according to the invention is liquid at 20° C.

Production of Ester Mixtures

The ester mixtures according to the invention can be obtained either by mixing single esters or ester mixtures so that mixtures according to formula (I) are obtained. Alternatively, the ester mixtures according to formula (I) can be obtained by esterifying the respective mixtures of carbon acids with the respective mixtures of alcohols. Likewise the ester mixtures according to formula (I) can be obtained by transesterification of the respective carbon acid methyl ester (mixtures) with the respective alcohol (mixtures).

The present invention also relates to a process for the production of ester mixtures of formula (I), $R_1$—C(=O)—O—$R_2$ wherein a carbon acid or a mixture of carbon acids $R_1$—COOH is reacted with an alcohol or a mixture of alcohols $R_2$—OH, wherein $R_1$ is an alkyl moiety with 7 to 9 carbon atoms and wherein $R_2$ is a an alkyl moiety with 8 to 10 carbon atoms, in such a ratio, that the resulting ester mixture comprises 5 to 60 weight-% of ester of the general formula (I), wherein $R_1$ is an alkyl moiety with 9 carbon atoms, based on the total amount of esters according to formula (I) and/or the mixture comprises 5 to 60 weight-% of ester of the general formula (I), wherein $R_2$ is an alkyl moiety with 10 carbon atoms, based on the total amount of esters according to formula (I). This can for example be achieved by reacting the respective amount of carbon acid (or carbon acid mixtures) with the respective amounts of alcohol (or alcohol mixtures) in equimolar amounts.

In a preferred embodiment of the invention, the mixture containing the carbon acid (or carbon acid mixture) and the alcohol (or alcohol mixture) is reacted in the presence of an esterification catalyst.

In a preferred embodiment of the invention, the mixture containing the carbon acid (or carbon acid mixture) and the alcohol (or alcohol mixture) is heated, the water formed is continuously removed and the crude product is then distilled. The process may be carried out in the presence of an esterification catalyst, for example an acid or a base. In a preferred embodiment, the process is carried out in the absence of solvents, preferably with educts which are substantially water-free. A preferred embodiment of the process is characterized by the use of a tin catalyst. Suitable tin catalysts are, for example, tin oxalate (for example Fascat® 2001), tin oxide (SnO, Fascat® 2000) and tin(IV) catalysts, such as dibutyl tin diacetate (Fascat® 4200), dibutyl tin oxide (Fascat® 4201) and dibutyl tin laurate (Fascat® 4202) or tin oxide (SnO) which were once marketed by Atofina, but are now marketed by Arkema. The esterification is preferably carried out at temperatures in the range from 100 to 300° C. and, more particularly, at temperatures in the range from 200 to 250° C.

In another embodiment, at least one enzyme is used as the catalyst. Suitable enzymes are any enzymes or enzyme mixtures known to the expert which are capable of catalyzing the esterification of alcohol and acid, for example lipases, acyl transferases and esterases. The enzyme-catalyzed esterification is typically carried out at temperatures of 20 to 100° C. and preferably at temperatures of 40 to 80° C.

The present invention also relates to a process for the production of ester mixtures for formula (I), $R_1$—C(=O)—O—$R_2$ wherein a carbon acid alkyl ester or a mixture of carbon acid alkyl esters $R_1$—C(=O)—$R_3$ are reacted with an alcohol or a mixture of alcohols $R_2$—OH, wherein $R_1$ is an alkyl moiety with 7 to 9 carbon atoms and wherein $R_2$ is an alkyl moiety with 8 to 10 carbon atoms wherein $R_3$ is an alkyl moiety with 1, 2, 3 or 4 carbon atoms, in the presence of a transesterification catalyst, in such a ratio, that the resulting ester mixture comprises 5 to 60 weight-% of ester of the general formula (I), wherein $R_1$ is an alkyl moiety with 9 carbon atoms, based on the total amount of esters according to formula (I) and/or the mixture comprises 5 to 60 weight-% of ester of the general formula (I), wherein $R_2$ is an alkyl moiety with 10 carbon atoms, based on the total amount of esters according to formula (I). In a preferred embodiment $R_3$ is selected from the group consisting of Methyl-, Ethyl-, n-Butyl.

The present invention also relates to a process for the production of ester mixtures of formula (I), $R_1$—C(=O)—O—$R_2$ wherein a carbon acid methyl ester or a mixture of carbon acid methyl esters $R_1$—C(=O)—$CH_3$ are reacted with an alcohol or a mixture of alcohols $R_2$—OH, wherein $R_1$ is an alkyl moiety with 7 to 9 carbon atoms and wherein $R_2$ is a an alkyl moiety with 8 to 10 carbon atoms in the presence of a transesterification catalyst, in such a ratio, that the resulting ester mixture comprises 5 to 60 weight-% of ester of the general formula (I), wherein $R_1$ is an alkyl moiety with 9 carbon atoms, based on the total amount of esters according to formula (I) and/or the mixture comprises 5 to 60 weight-% of ester of the general formula (I), wherein $R_2$ is an alkyl moiety with 10 carbon atoms, based on the total amount of esters according to formula (I).

This can for example be achieved by reacting the respective amount of carbon acid alkyl ester (or carbon acid alkyl ester mixtures) with the respective amounts of alcohol (or alcohol mixtures) in equimolar amounts.

In a preferred embodiment, the mixture containing the carbon acid alkyl ester (or carbon acid alkyl ester mixture) and the alcohol (or alcohol mixture) is heated in the presence of the transesterification catalyst, the water formed is continuously removed and the crude product is distilled. In a preferred embodiment, the process is carried out in the absence of solvents, preferably with educts which are substantially water-free. The transesterification is preferably carried out at temperatures of 100 to 300° C. and more particularly at temperatures of 200 to 250° C. The transesterification catalyst used may be selected from any of those known to the expert, sodium methylate or tetra-alkyl titanate being preferred.

In another embodiment, at least one enzyme is used as the catalyst. Suitable enzymes are any enzymes or enzyme mixtures known to the expert which are capable of catalyzing the transesterification of alcohol and acid methyl ester, for example lipases, acyl transferases and esterases. The enzyme-catalyzed transesterification is typically carried out at temperatures of 20 to 100° C. and preferably at temperatures of 40 to 80° C.

Cosmetic and/or Pharmaceutical Compositions

The ester mixture according to the invention can be suitably used in cosmetic and/or pharmaceutical composition. A further embodiment of the invention is therefore directed to a cosmetic and/or pharmaceutical composition comprising 0.1 to 95 weight-% of a mixture of esters according to the general formula (I), $R_1$—C(=O)—O—$R_2$, wherein $R_1$ is an alkyl moiety with 7 to 9 carbon atoms and wherein $R_2$ is a an alkyl moiety with 8 to 10 carbon atoms,
wherein the mixture comprises 5 to 60 weight-% of ester of the general formula (I), wherein $R_1$ is an alkyl moiety with 9 carbon atoms, based on the total amount of esters according to formula (I) and/or wherein the mixture comprises 5 to 60 weight-% of ester of the general formula (I), wherein $R_2$ is an alkyl moiety with 10 carbon atoms, based on the total amount of esters according to formula (I).

A further embodiment of the invention is therefore directed to the use of an ester mixture according to formula (I) for the preparation of or in cosmetic and/or pharmaceutical compositions, preferably as oil component and/or as solubilizer and/or as wetting agent.

The compositions according to the invention and the ester mixtures according to the invention are suitable for incorporation in all cosmetic preparations such as, for example, body care and cleansing preparations, such as body oil, baby oil, body milk, creams, lotions, sprayable emulsions, sunscreens, antiperspirants, liquid and bar soaps, etc. They may also be used in surfactant-containing formulations such as, for example, foam and shower baths, hair shampoos and hair care rinses. They may be applied as a care component to tissues, papers, wipes, nonwovens, sponges, puffs, plasters and bandages which are used in the field of hygiene and care (wet wipes for baby hygiene and baby care, cleaning wipes, facial wipes, skin care wipes, care wipes containing active ingredients against ageing of the skin, wipes containing sun protection formulations and insect repellents and wipes for decorative cosmetics or for after-sun treatment, toilet wipes, antiperspirant wipes, diapers, handkerchiefs, wet wipes, hygiene products, self-tanning wipes). They may also be used inter alia in hair-care, hair-cleaning or hair-coloring compositions. They may furthermore also be used in decorative cosmetics, such as lipsticks, lipglosses, foundations, make-up, pressed and loose powders, eye-shadow, mascaras and the like.

A further aspect of the invention is directed to the use of the ester mixtures according to the invention in cosmetic and/or pharmaceutical compositions for moistening or coating of substrates, which are used for cleaning and/or caring of the body and/or hair.

A further embodiment of the invention is directed to cosmetic and/or pharmaceutical compositions comprising
(a) 0.1 to 95 weight-% of a mixture of esters according to the general formula (I) $R_1$—C(=O)—O—$R_2$,
   wherein $R_1$ is an alkyl moiety with 7 to 9 carbon atoms and
   wherein $R_2$ is a an alkyl moiety with 8 to 10 carbon atoms,
   wherein the mixture comprises 5 to 60 weight-% of ester of the general formula (I), wherein $R_1$ is an alkyl moiety with 9 carbon atoms, based on the total amount of esters according to formula (I) and/or
   wherein the mixture comprises 5 to 60 weight-% of ester of the general formula (I), wherein $R_2$ is an alkyl moiety with 10 carbon atoms, based on the total amount of esters according to formula (I).
(b) at least surface-active substance (b-1) and/or at least one wax component (b-2) and/or at least one polymer (b-3) and/or at least one other oil component (b-4).

The compositions according to the invention preferably contain 0.1 to 80 weight-%, more particularly 0.5 to 70 weight-%, preferably 0.75 to 60 weight-%, more particularly 1 to 50 weight-%, preferably 1 to 40 weight-% of an ester mixture according to formula (I).

The present invention also relates to cosmetic and/or pharmaceutical compositions containing
(a) 0.1 to 95 weight-%, more particularly 0.1 to 80 weight-%, more particularly 0.1 to 70 weight-%, preferably 0.1 to 60 weight-%, more particularly 0.1 to 50 weight-%, preferably 0.1 to 40 weight-% of an ester mixture according to formula (I)
(b) 0.1 to 20 weight-% surface-active substance (b-1) and/or wax component (b-2) and/or polymer (b-3), 0.1 to 40% by weight of other oil components (b-4) and
(c) 0 to 98% by weight of water.

All percentages by weight represent weight-%, based on the cosmetic and/or pharmaceutical composition, unless otherwise stated.

Surface-Active Substances

In one embodiment of the invention, the compositions according to the invention contain at least one surface-active substance. Surface-active substances are all substances which lower the interfacial tension between the aqueous and the non-aqueous phase. Surface-active substances include emulsifiers and surfactants.

In one embodiment of the invention, the composition according to the invention contains more than one surface-active substance. Depending on the other components, the expert uses typical systems (such as, for example, emulsifier and co-emulsifier).

The compositions according to the invention can contain the surface-active substance(s) in a quantity of 0 to 80 weight-%, preferably 0.1 0 to 40 weight-%, preferably 0.1 to 20 weight-%, preferably 0.1 to 15 weight-% and more particularly 0.1 to 10 weight-%, based on the total weight of the composition.

A suitable emulsifier is in principle any surface-active substance, but in particular substances with an HLB value of from 1 to 20 according to the Griffin scale. Each emulsifier is assigned a so-called HLB value (a dimensionless number between 1 and 20, Griffin scale) which indicates whether a preferred solubility in water or oil is present. Numbers below 9 indicate preferably oil-soluble, hydrophobic emulsifiers; numbers above 11 water-soluble, hydrophilic emulsifiers. The HLB value says something about the equilibrium of the size and strength of the hydrophilic and of the lipophilic groups in an emulsifier. The Griffin scale is described in W C Griffin, J. Soc. Cosmet. Chem. 1 (1949) 311; W C Griffin, J. Soc. Cosmet. Chem. 5 (1954) 249.

The HLB value of an emulsifier can also be calculated from increments, where the HLB increments for the various hydrophilic and hydrophobic groups from which a molecule is composed. As a rule, it can be found in tables (e.g. H. P. Fiedler, Lexikon der Hilfsstoffe für Pharmazie, Kosmetik and angrenzende Gebiete [Lexion of Auxiliaries for Pharmacy, Cosmetics and Related Fields], Editio Cantor Verlag, Aulendorf, 4th edition, 1996) or the manufacturers' information. The solubility of the emulsifier in the two phases practically determines the type of emulsion. If the emulsifier is more soluble in water, then an O/W emulsion is obtained. By contrast, if the emulsifier has better solubility in the oil phase, then under otherwise identical preparation conditions, a W/O emulsion is formed.

Nonionic Emulsifiers

The group of nonionic emulsifiers includes, for example,
(1) products of the addition of 2 to 50 mol ethylene oxide and/or 1 to 20 mol propylene oxide onto linear fatty alcohols containing 8 to 40 carbon atoms, onto fatty acids containing 12 to 40 carbon atoms and onto alkylphenols containing 8 to 15 carbon atoms in the alkyl group;
(2) $C_{12-18}$ fatty acid monoesters and diesters of products of the addition of 1 to 50 mol ethylene oxide onto glycerol;
(3) sorbitan monoesters and diesters of saturated and unsaturated fatty acids containing 6 to 22 carbon atoms and ethylene oxide adducts thereof;
(4) alkyl mono- and oligoglycosides containing 8 to 22 carbon atoms in the alkyl group and ethoxylated analogs thereof;
(5) products of the addition of 7 to 60 mol ethylene oxide onto castor oil and/or hydrogenated castor oil;
(6) polyol esters and, in particular, polyglycerol esters such as, for example, polyolpoly-12-hydroxystearate, polyglycerol polyricinoleate, polyglyceryl-4-laurate, polyglycerol diisostearate or polyglycerol dimerate. Mixtures of compounds from several of these classes are also suitable;
(7) products of the addition of 2 to 15 mol ethylene oxide onto castor oil and/or hydrogenated castor oil;
(8) partial esters based on linear, branched, unsaturated or saturated $C_{6-22}$ fatty acids, ricinoleic acid and 12-hydroxystearic acid and polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose) or mixed esters as well as sucrose polystearate (commercially available as Emulgade® SUCRO from Cognis).
(9) polysiloxane/polyalkyl polyether copolymer or corresponding derivatives;
(10) mixed esters of pentaerythritol, fatty acids, citric acid and fatty alcohol and/or mixed esters of fatty acids containing 6 to 22 carbon atoms, methyl glucose and polyols, preferably glycerol or polyglycerol.

The addition products of ethylene oxide and/or propylene oxide onto fatty alcohols, fatty acids, alkylphenols, glycerol monoesters and diesters and sorbitan monoesters and diesters of fatty acids or onto castor oil are known commercially available products. They are homolog mixtures of which the average degree of alkoxylation corresponds to the ratio between the quantities of ethylene oxide and/or propylene oxide and substrate with which the addition reaction is carried out. These emulsifiers are w/o or o/w emulsifiers, depending on the degree of ethoxylation. $C_{12/18}$ fatty acid monoesters and diesters of addition products of ethylene oxide onto glycerol are known as lipid layer enhancers for cosmetic compositions.

According to the invention, particularly suitable and mild emulsifiers are the polyol poly-12-hydroxystearates and mixtures thereof marketed by Cognis Deutschland GmbH under the name of "Dehymuls® PGPH" (w/o emulsifier) or "Eumulgin® VL 75" (mixture with Coco Glucosides in a ratio by weight of 1:1, o/w emulsifier) or "Dehymuls® SBL" (w/o emulsifier). Particular reference is made in this connection to EP 0 766 661 B1. The polyol component of these emulsifiers may be derived from substances which contain at least two, preferably 3 to 12 and more particularly 3 to 8 hydroxyl groups and 2 to 12 carbon atoms.

In principle, suitable lipophilic w/o emulsifiers are emulsifiers with an HLB value of 1 to 8 which are listed in numerous Tables and are well-known to the expert. Some of these emulsifiers are listed, for example, in Kirk-Othmer, "Encyclopedia of Chemical Technology", 3rd Edition, 1979, Vol. 8, page 913. The HLB value for ethoxylated products may also be calculated to the following formula: HLB=(100−L):5, where L is the percentage by weight of lipophilic groups, i.e. fatty alkyl or fatty acyl groups, in percent by weight in the ethylene oxide adducts.

Of particular advantage from the group of w/o emulsifiers are partial esters of polyols, more particularly $C_{4-6}$ polyols, such as for example partial esters of pentaerythritol or sugar esters, for example sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable emulsifiers.

Depending on the formulation, it can also be of advantage additionally to use at least one emulsifier from the group of nonionic o/w emulsifiers (HLB value: 8-18) and/or solubilizers. Examples of such emulsifiers are the ethylene oxide adducts mentioned at the beginning with a correspondingly high degree of ethoxylation, for example 10-20 ethylene oxide units for o/w emulsifiers and 20-40 ethylene oxide units for so-called solubilizers. Particularly advantageous o/w emulsifiers for the purposes of the invention are Ceteareth-12, Cetheareth-20 and PEG-20 Stearate. Particularly suitable solubilizers are Eumulgin® HRE 40 (INCI name: PEG-40 Hydrogenated Castor oil), Eumulgin® HRE 60 (INCI name: PEG-60 Hydrogenated Castor Oil), Eumulgin® L (INCI name: PPG-1-PEG-9 Laurylglycolether) and Eumulgin® SML 20 (INCI name: Polysorbat-20).

Nonionic emulsifiers from the group of alkyl oligoglycosides are particularly compatible with the skin. $C_{8-22}$ alkyl mono- and oligoglycosides, their production and their use are known from the prior art. They are produced in particular by reacting glucose or oligosaccharides with primary alcohols containing 6 to 24, preferably 8 to 22 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based. Products available under the name of Plantacare® or Plantaren® contain a $C_{8-16}$ alkyl group attached by a glucosidic bond to an oligoglucoside unit with an average degree of oligomerization of 1 to 2. The acyl glucamides derived from glucamine are also suitable nonionic emulsifiers. The product marketed under the name of Emulgade® PL 68/50 by Cognis Deutschland GmbH, which is a 1:1 mixture of alkyl polyglucosides and fatty alcohols, is preferred for the purposes of the invention. According to the invention, the mixture of Lauryl Glucoside, Polyglyceryl-2-Dipolyhydroxystearate, glycerol and water which is marketed as Eumulgin® VL 75 may also be used with advantage in accordance with the invention.

Other suitable emulsifiers are such substances as lecithins and phospholipids. Examples of natural lecithins are the kephalins which are also known as phosphatidic acids and which are derivatives of 1,2-diacyl-sn-glycerol-3-phosphoric acids. By contrast, phospholipids are generally understood to be mono- and preferably diesters of phosphoric acid with glycerol (glycerophosphates) which are generally classed as fats. Sphingosines and sphingolipids are also suitable as fat-like substances.

Silicone emulsifiers, for example, may be present as emulsifiers. These can be selected, for example, from the group of alkylmethicone copolyols and/or alkyldimethicone copolyols, in particular from the group of compounds which are characterized by the following chemical structure:

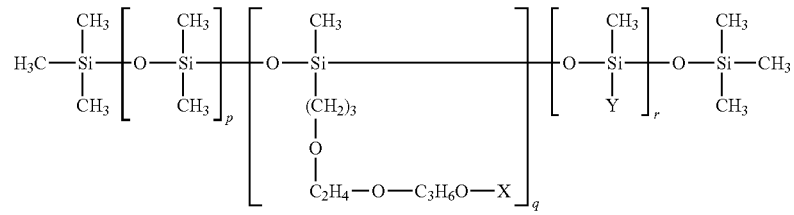

in which X and Y, independently of one another, are selected from the group H (hydrogen) and the branched and unbranched alkyl groups, acyl groups and alkoxy groups having 1-24 carbon atoms, p is a number from 0-200, q is a number from 1-40, and r is a number from 1-100.

One example of silicone emulsifiers to be used particularly advantageously within the context of the present invention are dimethicone copolyols, which are sold by Evonik Goldschmidt under the trade names ABIL® B 8842, ABIL® B 8843, ABIL® B 8847, ABIL® B 8851, ABIL® B 8852, ABIL® B 8863, ABIL® B 8873 and ABIL® B 88183.

A further example of interface-active substances to be used particularly advantageously within the context of the present invention is cetyl PEG/PPG-10/1 dimethicone (Cetyl Dimethiconecopolyol), which is sold by Evonik Goldschmidt under the trade name ABIL® EM 90.

A further example of interface-active substances to be used particularly advantageously within the context of the present invention is the cyclomethicone dimethiconecopolyol, which is sold by Evonik Goldschmidt under the trade name ABIL® EM 97 and ABIL® WE 09.

Furthermore, the emulsifier Lauryl PEG/PPG-18/18 Methicone (laurylmethicone copolyol) has proven to be very particularly advantageous and is available under the trade name Dow Corning® 5200 Formulation Aid from Dow Corning Ltd. Furthermore a silicone emulsifier with the INCI name "Cyclopentasiloxane and PEG/PG-18-18 Dimethicone" has proven to be advantageous, it is available for example under the tradename Dow Corning® 5225 C Formulation Aid.

A further advantageous silicone emulsifier is Octyl Dimethicone Ethoxy Glucoside from Wacker. For a water-in-silicone oil emulsion according to the invention, all known emulsifiers used for this type of emulsion can be used. According to the invention, particularly preferred water-in-silicone emulsifiers here are cetyl PEG/PPG-10/1 dimethicones and lauryl PEG/PPG-18/18 methicones [e.g. ABIL® EM 90 (Evonik Goldschmidt), DC5200 Formulation Aid (Dow Corning)] and any desired mixtures of the two emulsifiers.

A suitable anionic O/W emulsifier is for example Disodium Cetearyl Sulfosuccinate (commercially available under the tradename Eumulgin® Prisma).

Surfactant(s)

In one embodiment of the invention, the compositions according to the invention contain as surface-active substance at least one surfactant. The surfactant(s) may be selected from anionic, nonionic, cationic and/or amphoteric or zwitterionic surfactants. Surfactant-containing cosmetic compositions, such as for example shower gels, foam baths, shampoos, etc., preferably contain at least one anionic surfactant.

Typical examples of nonionic surfactants are fatty alcohol polyglycol ethers, alkylphenol polyglycol ethers, fatty acid polyglycol ethers, fatty acid amide polyglycol ethers, fatty amine polyglycol ethers, alkoxylated triglycerides, mixed ethers and mixed formals, optionally partly oxidized alk(en)yl oligoglycosides or glucuronic acid derivatives, fatty acid-N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution.

Zwitterionic surfactants are surface-active compounds which contain at least one quaternary ammonium group and at least one —COO$^{(-)}$ or —SO$_3$$^{(-)}$ group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable, particularly as co-surfactants. Ampholytic surfactants are surface-active compounds which, in addition to a $C_{8-18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids (commercially available under the tradename Dehyton® DC), N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Suitable are furthermore N-alkyliminodipropionic acid derivatives such as Sodium N-Lauryl-beta-Iminodipropionate, commercially available under the tradename Deriphat® 160 C. Suitalbe are furthermore Amphoacetates such as e.g. Cocoamphoacetates (e.g. Dehyton® MC) or Cocoamphodiacetates (e.g. Dehyton® DC).

Anionic surfactants are characterized by a water-solubilizing anionic group such as, for example, a carboxylate, sulfate, sulfonate or phosphate group and a lipophilic group. Dermatologically safe anionic surfactants are known to the expert in large numbers from relevant textbooks and are commercially available. They are, in particular, alkyl sulfates in the form of their alkali metal, ammonium or alkanolammonium salts, alkylether sulfates, alkylether carboxylates, acyl isethionates, acyl sarcosinates, acyl taurines containing linear $C_{12-18}$ alkyl or acyl groups and sulfosuccinates and acyl glutamates in the form of their alkali metal or ammonium salts. Particularly suitable anionic surfactants are Glyceryl stearate citrate (commercially available as Imwitor® 370, Imwitor® 372P, Axol® C62 or Dracorin® CE 614035) and/or glyceryl stearate lactate. Examples of suitable alkyl sulfates are for example Sodium Cetearyl Sulfate (commercially available as Lanette® E), examples of suitable phosphates are Potassium Cetyl Phosphate (commercially available as Amphisol® K).

Examples of suitable acyl glutamates are Sodium Stearoyl Glutamate (commercially available as Eumulgin® SG). A further example of a suitable anionic surfactant is Sodium Lauryl Glucose Carboxylate (commercially available as Plantapon® LGC).

Particularly suitable cationic surfactants are quaternary ammonium compounds, preferably ammonium halides, more especially chlorides and bromides, such as alkyl trimethyl ammonium chlorides, dialkyl dimethyl ammonium chlorides and trialkyl methyl ammonium chlorides, for example cetyl trimethyl ammonium chloride, stearyl trimethyl ammonium chloride, distearyl dimethyl ammonium chloride, lauryl dimethyl ammonium chloride, lauryl dimethyl benzyl ammonium chloride and tricetyl methyl ammonium chloride. Suitable are furthermore pseudo cationic surfactants such as stearylaminopropyl ditmethylamine (commercially available under the tradename Dehyquart® S 18 or Incromine® SB or TegoAmide S 18). In addition, the readily biodegradable quaternary ester compounds, such as for example the dialkyl ammonium methosulfates and methyl hydroxyalkyl dialkoyloxyalkyl ammonium methosulfates marketed under the name of Stepantex® and the corresponding products of the Dehyquart® series, may be used as cationic surfactants. "Esterquats" are generally understood to be quaternized fatty acid triethanolamine ester salts. They can provide the compositions with particular softness. They are known substances which are prepared by the relevant methods of organic chemistry. Other cationic surfactants suitable for use in accordance with the invention are the quaternized protein hydrolyzates. Suitable cationic surfactants are for example Dipalmitoylethyl Hydroxyethylmonium Methosulfate (tradename Dehyquart® C4046), Distearoylethyl Hydroxyethylmonium Methosulfate (tradename Dehyquart® F75), Dicocoylethyl Hydroxyethylmonium Methosulfate (tradename Dehyquart® L80), Behentrimonium Chloride (tradename Varisoft® BT), Distearyldimonium Chloride (tradename Varisoft® TA 100), Palmitamidopropyltrimonium Chloride (tradename Varisoft® PATC).

Wax Component b-2)

In one embodiment of the invention, the preparations according to the invention contain at least one wax component. The compositions according to the invention can contain the wax component(s) in a quantity of 0 to 40 weight-%, more particularly 0 to 20 weight-%, preferably 0.1 to 15 weight-% and more particularly 0.1 to 10 weight-%, based on the total weight of the composition.

Waxes are normally understood to be natural or synthetic substances and mixtures having the following properties: they have a solid to brittle hard consistency, are coarsely to finely crystalline, transparent to opaque and melt above 30° C. without decomposing. Even slightly above their melting point, they are low in viscosity and non-stringing and are very temperature-dependent in their consistency and solubility. A single wax component or a mixture of wax components melting at or above 30° C. may be used in accordance with the invention.

According to the invention, fats and fat-like substances with a wax-like consistency may also be used as waxes providing they have the required melting point. These include inter alia fats (triglycerides), mono- and diglycerides, natural and synthetic waxes, fat and wax alcohols, fatty acids, esters of fatty alcohols and fatty acids and fatty acid amides or mixtures of these substances.

Fats in the context of the invention are understood to be triacylglycerols, i.e. the triple esters of fatty acids with glycerol. The triacylglycerols preferably contain saturated, unbranched and unsubstituted fatty acid components. They may also be mixed esters, i.e. triple esters of glycerol with various fatty acids. So-called hardened fats and oils obtained by partial hydrogenation may be used in accordance with the invention and are particularly suitable as consistency factors. Vegetable hardened fats and oils, for example hardened castor oil, peanut oil, soybean oil, colza oil, rapeseed oil, cottonseed oil, soybean oil, sunflower oil, palm oil, palm kernel oil, linseed oil, almond oil, corn oil, olive oil, sesame oil, cocoa butter and coconut fat, shea butter are preferred.

Suitable fats are inter alia the triple esters of glycerol with $C_{12-60}$ fatty acids and in particular $C_{12-36}$ fatty acids. These include hydrogenated castor oil, a triple ester of glycerol and a hydroxystearic acid which is marketed, for example, under the name of Cutina® HR. Glycerol tristearate, glycerol tribehenate (for example Syncrowax® HRC), glycerol tripalmitate or the triglyceride mixtures known under the name of Syncrowax® HGLC are also suitable providing the melting point of the wax component or the mixture is 30° C. or higher.

According to the invention, suitable wax components are, in particular, mono- and diglycerides and mixtures of these partial glycerides. Glyceride mixtures suitable for use in accordance with the invention include the products Novata® AB and Novata® B (mixture of C12-18 mono-, di- and triglycerides) and Cutina® HVG (Hydrogenated Vegetable Glycerides) or Cutina® GMS (glyceryl stearate) marketed by Cognis GmbH.

The fatty alcohols suitable for use as a wax component in accordance with the invention include $C_{12-50}$ fatty alcohols.

The fatty alcohols may be obtained from natural fats, oils and waxes such as, for example, myristyl alcohol, 1-pentadecanol, cetyl alcohol, 1-heptadecanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, saturated unbranched fatty alcohols are preferred. However, unsaturated, branched or unbranched fatty alcohols may also be used as the wax component in accordance with the invention providing they have the required melting point. Other suitable fatty alcohols are the fatty alcohol cuts obtained in the reduction of naturally occurring fats and oils such as, for example, bovine tallow, peanut oil, colza oil, cottonseed oil, soybean oil, sunflower oil, palm kernel oil, linseed oil, castor oil, corn oil, rapeseed oil, sesame oil, cocoa butter and coconut oil. However, synthetic alcohols, for example the linear, even-numbered fatty alcohols from Ziegler's synthesis (Alfols) or the partly branched alcohols from the oxosynthesis (Dobanols) may also be used. $C_{14-22}$ fatty alcohols marketed for example by Cognis Deutschland GmbH under the name of Lanette® 16 ($C_{16}$ alcohol), Lanette® 14 ($C_{14}$ alcohol), Lanette® O ($C_{16/18}$ alcohol) and Lanette® 22 ($C_{18/22}$ alcohol) are particularly suitable for the purposes of the invention. Fatty alcohols give the compositions a dryer feeling on the skin than triglycerides.

$C_{14-40}$ fatty acids or mixtures thereof may also be used as wax components. These include, for example, myristic, pentadecanoic, palmitic, margaric, stearic, nonadecanoic, arachic, behenic, lignoceric, cerotic, melissic, erucic and elaeostearic acid and substituted fatty acids such as, for example, 12-hydroxystearic acid, and the amides or monoethanolamides of the fatty acids. This list is meant to be purely exemplary without any limiting character.

Waxes suitable for use in accordance with the invention are, for example, natural vegetable waxes, such as candelilla wax, carnauba wax, Japan wax, espartograss wax, cork wax, guaruma wax, rice oil wax, sugar cane wax, ouricury wax, montan wax, sunflower wax, fruit waxes, such as orange waxes, lemon waxes, grapefruit wax, bayberry wax, and animal waxes such as, for example, beeswax, shellac wax, spermaceti, wool wax and uropygial fat. According to the invention, it can be of advantage to use hydrogenated or hardened waxes. Natural waxes usable in accordance with the invention also include the mineral waxes, such as ceresine and ozocerite for example, or the petrochemical waxes, for example petrolatum, paraffin waxes and microwaxes. Other suitable wax components are chemically modified waxes, more particularly the hard waxes such as, for example, montan ester waxes, sasol waxes and hydrogenated jojoba waxes. Synthetic waxes usable in accordance with the invention include, for example, wax-like polyalkylene waxes and polyethylene glycol waxes. Vegetable waxes are preferred for the purposes of the invention.

The wax component may also be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (for example 12-hydroxystearic acid) and saturated and/or unsaturated, branched and/or unbranched alcohols and also from the group of lactides of long-chain hydroxycarboxylic acids. Examples of esters such as these include, for example, $C_{16-40}$ alkyl stearates, $C_{20-40}$ alkyl stearates (for example Kesterwachs® K82H), $C_{20-40}$ dialkyl esters of dimer acids, $C_{18-35}$ alkyl hydroxystearoyl stearates or $C_{20-40}$ alkyl erucates. Other suitable wax components which may be used are $C_{30}$-

50 alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

Polymers b-3)

In one embodiment of the invention, the compositions according to the invention contain at least one polymer. The compositions according to the invention can contain the polymer(s) in a quantity of 0 to 20 weight-%, preferably 0.05 to 18 weight-%, preferably 0.05 to 15 weight-%, and, more particularly, 0.05 to 10 weight-%, more preferably 0.1 to 1 weight-%, based on the total weight of the composition. In a preferred embodiment of the invention, the polymers can be present in an amount of 0.1 to 5 weight-%, preferably 0.1 to 3 weight-% especially 0.1 to 2 weight-% based on the total weight of the composition.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohydroxypropyl diethylenetriamine (Cartaretine®, Sandoz), copolymers of acrylic acid with dimethyl diallyl ammonium chloride (Merquat® 550, Chemviron), polyaminopolyamides, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Especially suitable are anionic polymers with the INCI name Carbomer, like for example Carbopol of types 980, 980, 981, 1382, 2984, 5984 as well as Rheocare® C plus and Rheocare® 400). Further suitable anionic polymers are those with the INCI name Acrylates/C10-30 Alkyl Acrylate Crosspolymer (e.g. Pemulen® TR, Pemulen® TR 2, Carbopol® Ultrez), Acrylates Copolymer (e.g. Rheocare TTA, TTN, TTN-2), Acrylamide/Sodium Acrylate Copolymer (e.g. Cosmedia® ATC), Sodium Polyacrylate (e.g. Cosmedia® ATH, Cosmedia® SP), Polyacrylamides (e.g. Sepigel® 305 or Sepigel® 501). Preferred anionic polymers are Polyacrylic acid homo and co-polymers.

Further suitable polymers are silicione elastomer gums, like for example silicone elastomer blends, such as blends with the INCI name Cyclolpentasiloxane (and) Dimethiconol (and) Dimethicone Crosspolymer, commercially available as Dow Corning® DC 9027, blends with the INCI name Isodecyl neopentanoate (and) Dimethicone/bis-isobutyl PPG-20 Crosspolymer, commercially available as Dow Corning® DC EL 8051 IN, blends with the INCI name Dimethicone/Vinyl Dimethicone Crosspolymer (and) C12-14 Pareth-12), commercially available as Dow Corning® DC 9509, and blends with the INCI name Dimethicone/Vinyl Dimethicone Crosspolymer (and) Silica, commercially available as Dow Corning® DC 9701 Cosmetic Powder.

Other suitable polymers are polysaccharides, more particularly xanthan gum, guar gum, agar agar, alginates and tyloses as well as tara gum, carraghenane, sclerotium gum and natural cellulose.

Other Oil Components b-4)

The cosmetic compositions according to the invention can contain—in addition to the ester mixture according to formula (I) other oil components. The total oil components (esters according to the invention plus other oil components) are typically present in a total quantity of 0.1 to 95, preferably of 0.1 to 80, more particularly 0.5 to 70, preferably 1 to 60, more particularly 1 to 50 weight-%, more particularly 1 to 40 weight-%, preferably 5 to 25 weight-% and more particularly 5 to 15 weight-%. The other oil components are typically present in a quantity of 0.1 to 40 weight-%.

The other oil components may be selected, for example, from Guerbet alcohols based on fatty alcohols containing 6 to 18 and preferably 8 to 10 carbon atoms and other additional esters, such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18-38}$ alkylhydroxycarboxylic acids with linear or branched $C_{6-22}$ fatty alcohols, more especially Dioctyl Malate, esters of linear and/or branched fatty acids with polyhydric alcohols (for example propylene glycol, dimer diol or trimer triol), triglycerides based on $C_{6-10}$ fatty acids, liquid mono-, di- and triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with polyols containing 2 to 10 carbon atoms and 2 to 6 hydroxyl groups, vegetable oils, branched primary alcohols, substituted cyclohexanes, linear and branched $C_{6-22}$ fatty alcohol carbonates such as, for example, Dicaprylyl Carbonate (Cetiol® CC), Guerbet carbonates based on fatty alcohols containing 6 to 18 and preferably 8 to 10 carbon atoms, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group such as, for example, Dicaprylyl Ether (Cetiol® OE), ring opening products of epoxidized fatty acid esters with polyols and hydrocarbons or mixtures thereof thereof. Also suitable are esters of 2-propylheptanol with n-octanoic acid, a product which is commercially available under the tradename Cetiol® Sensoft (Cognis GmbH). Also suitable are hydrocarbons, such as for example undecan and tridecan. Also suitable are alkanes, such as for example INCI Conocnut/Palm/Palm Kernel Oil Alkanes, commercially available as Vegelight 1214 from Biosynthesis).

A further embodiment of the present invention is directed to cosmetic and/or pharmaceutical compositions containing
(a) 0.1 to 95 weight-%, more particularly 0.1 to 80 weight-%, more particularly 0.1 to 70 weight-%, preferably 0.1 to 60 weight-%, more particularly 0.1 to 50 weight-%, preferably 0.1 to 40 weight-% of an ester mixture according to formula (I)
(b) at least one UV protective factor.

UV Protective Factor

UV photoprotective factors are, for example, to be understood as meaning organic substances (photoprotective filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

3-benzylidenecamphor (Mexoryl® SD) or 3-benzylidenenorcamphor (Mexoryl® SDS 20) and derivatives thereof, e.g. 3-(4-methylbenzylidene)camphor 3-(4'-Trimethylammonium)benzyliden-bornan-2-on-methylsulfat (Mexoryl® SO)

3,3'-(1,4-Phenylendimethin)-bis(7,7-dimethyl-2-oxobicyclo-[2.2.1]heptan-1-methansulfonsäure) and salts (Mexoryl® SX)

3-(4'-Sulfo)-benzyliden-bornan-2-on and salts (Mexoryl® SL)

Polymer of N-{(2 und 4)-[2-oxoborn-3-yliden) methyl}benzyl]acrylamid (Mexoryl® SW)

2-(2H-Benzotriazol-2-yl)-4-methyl-6-(2-methyl-3-(1,3,3, 3-tetramethyl-1-(trimethylsilyloxy) disiloxanyl)propyl) phenol (Mexoryl® XL)

4-aminobenzoic acid derivatives, preferably 2-ethylhexyl 4-(dimethylamino)benzoate, 2-octyl 4-(di-methylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomethyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzalmalonate;

triazine derivatives, such as, for example, 2,4,6-trianilino (p-carbo-2'-ethyl-1-hexyloxy)-1,3,5-triazine, or 2,4,6-Tris[p-(2-ethylhexyl-oxycar-bonyl)anilino]-1,3,5-triazin (Uvinul® T 150) or octyltriazone or (Uvasorb® HEB); or diethylhexyl butamido triazone (Uvasorb® HEB; =4,4'-[(6-[4-((1,1-Dimethylethyl)amino-carbonyl)phenyl-amino]-1,3,5-triazin-2,4-diyl)diimino]bis (benzoesäure-2-ethylhexylester)

2,2(-Methylen-bis(6-(2H-benzotriazol-2-yl)-4-(1,1,3,3-tetramethyl-butyl)phenol) (Tinosorb® M);

2,4-Bis[4-(2-ethylhexyloxy)-2-hydroxyphenyl]-6-(4-methoxyphenyl)-1,3,5-triazin (Tinosorb® S);

propane-1,3-diones, such as, for example, 1-(4-tert-butylphenyl)-3-(4'-methoxyphenyl)propane-1,3-dione;

ketotricyclo(5.2.1.0)decane derivatives, as disclosed in EP 0694521 B1.

Suitable water-soluble substances are:

2-phenylbenzimidazole-5-sulphonic acid and the alkali metal, alkaline earth metal, ammonium, alkylammonium, alkanolammonium and glucammonium salts thereof;

2,2(-(1,4-Phenylen)bis(1H-benzimidazol-4,6-disulfonic acid, monosodium salt) (Neo Heliopan® AP) (INCI: Disodium Phenyl Dibenzimidazole Tetrasulfonate)

sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidene-methyl)benzenesulphonic acid and 2-methyl-5-(2-oxo-3-bornylidene)sulphonic acid and salts thereof.

In a preferred embodiment of the invention the compositions comprise at least one oil-soluble UV protective factor and at least one water-soluble UV protective factor.

Suitable typical UV-A filters are, in particular, derivatives of benzoylmethane, such as, for example, 1-(4'-tert-buty)phenyl)-3-(4'-methoxyphenyl)propane-1,3-dione, 4-tert-butyl-4'-methoxydibenzoyl-methane (Parsol® 1789), 1-phenyl-3-(4'-isopropylphenyl)propane-1,3-dione, and enamine compounds, as disclosed in DE 19712033 A1 (BASF) as well as Benzoic Acid, 2-[4-(Diethylamino)-2-Hydroxybenzoyl]-, Hexyl Ester (Uvinul® A plus, INCI: Diethylamino hydroxybenzoyl hexyl benzoate. The UV-A and UV-B filters can of course also be used in mixtures. Particularly favourable combinations consist of the derivatives of benzoylmethane, e.g. 4-tert-butyl-4'-methoxydi-benzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts.

Suitable UV-photoprotective factors are especially the ones listed in Annex VII of the Commissions Directive (in the Version Commission Directive 2005/9/EC of 28 Jan. 2005 amending Council Directive 76/768/EEC, concerning cosmetic products, for the purposes of adapting Annexes VII thereof to technical progress), which are hereby explicitly referred to.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 Eusolex® T-Aqua, Eusolex® AVO, Eusolex® T-ECO, Eusolex® T-OLEO and Eusolex® T-S (Merck). Typical examples of zinc oxides are for example Zinc Oxide neutral, Zinc Oxide NDM (Symrise) or Z-Cote® (BASF) or SUNZnO-AS as well as SUNZnO-NAS (Sunjun Chemical Co. Ltd.). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide.

Further suitable UV protective factors listed in the review of P. Finkel in SÖFW-Journal 122, 8/1996, p. 543 to 548 as well as in Parf. Kosm. 80. Jahrgang, Nr. 3/1999, p. 10 to 16 are hereby included by reference.

Besides the two groups of primary UV protection factors mentioned above, secondary UV protection factors of the antioxidant type may also be used. Secondary UV protection factors of the antioxidant type interrupt the photochemical reaction chain which is initiated when UV rays penetrate into the skin.

In a preferred embodiment of the invention, the compositions comprise at least one UV protective factor selected from the group consisting of
- 4-Methylbenzylidene Camphor (Tradename: NeoHeliopan® MBC, supplier: Symrise);
- Benzophenone-3 (Tradename: NeoHeliopan® BB, supplier: Symrise);
- Butyl Methoxydibenzoylmethane (Tradename: Parsol® 1789, Hoffmann-La Roche
- Bis-Ethylhexyloxyphenol Methoxyphenyl Triazine (Tradename: Tinosorb® S, CIBA),
- Methylene Bis-Benzotriazolyl Tetramethylbutylphenol (Tradename: Tinosorb® M, supplier: Ciba Specialty Chemicals Corporation;
- Diethylhexyl Butamido Triazone (Tradename: Uvasorb® HEB, supplier: 3V Inc.;
- Ethylhexyl Triazone (Tradename: Uvinul® 150, supplier: BASF AG;
- Diethylamino Hydroxybenzoyl Hexyl Benzoate (Tradename: Uvinul® A plus, BASF SE;
- 3-(4'-Trimethylammonium) benzyliden-bornan-2-on-methylsulfat (Tradename: Mexoryl® SO; INCI Camphor Benzalkonium Methosulfate)
- 3,3'-(1,4-Phenylendimethin)-bis(7,7-dimethyl-2-oxobicyclo-[2.2.1]heptan-1-methan-sulfonic acid (Mexoryl® SX, INCI Terephthalylidene Dicamphor Sulfonic Acid),
- 3-(4'-Sulfo)-benzyliden-bornan-2-on, (Mexory® SL; Benzylidene Camphor Sulfonic Acid)
- Polymer of N-{(2 and 4)-[2-oxoborn-3-yliden) methyl}benzyl]acrylamid (Tradename: Mexoryl® SW, INCI Polyacrylamidomethyl Benzylidene Camphor)
- 2-(2H-Benzotriazol-2-yl)-4-methyl-6-(2-methyl-3-(1,3,3,3-tetramethyl-1-(trimethylsilyloxy) disiloxanyl)propyl) phenol (INCI: Drometrizole Trisiloxane) and
- Dimethicodiethylbenzalmalonate (Tradename: Parsol® SLX, INCI Polysilicone-15).

The compositions according to the invention can comprise the UV photoprotective factors in an amount of 0.1 to 30 weight-%, preferably 2.5 to 20 Gew.-%, more preferably 5-15 weight-%, based on the cosmetic and/or pharmaceutical composition.

Auxiliaries and Additives

Depending on the application envisaged, the cosmetic compositions contain a number of other auxiliaries and additives such as, for example, consistency factors, thickeners, superfatting agents, stabilizers, polymers, phospholipids, biogenic agents, antioxidants, deodorants, antiperspirants, antidandruff agents, film formers, swelling agents, insect repellents, self-tanning agents, tyrosinase inhibitors (depigmenting agents), fillers, hydrotropes, solubilizers, preservatives, perfume oils, dyes, etc. which are listed by way of example in the following.

Suitable thickeners are, for example, Aerosil® types (hydrophilic silicas), carboxymethyl cellulose and hydroxyethyl and hydroxypropyl cellulose, polyvinyl alcohol, polyvinyl pyrrolidone and bentonites, for example Bentone® Gel VS-5PC (Rheox).). A suitable thickener is also the product which is sold under the tradename Cosmedia® Gel CC (Cognis GmbH), which is a mixture of Dicaprylyl Carbonate, Stearalkonium Hectorite and Propylene Carbonate. In the context of the invention, biogenic agents are, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, for example prunus extract, bambara nut extract, and vitamin complexes. Deodorizing components counteract, mask or eliminate body odors. Body odors are formed through the action of skin bacteria on apocrine perspiration which results in the formation of unpleasant-smelling degradation products. Accordingly, suitable deodorizing components are inter alia germ inhibitors, enzyme inhibitors, odor absorbers or odor maskers. Suitable insect repellents are N,N-diethyl-m-toluamide, pentane-1,2-diol or 3-(N-n-butyl-N-acetylamino)-propionic acid ethyl ester), which is marketed as Insect Repellent 3535 by Merck KGaA, and Butylacetylaminopropionate. A suitable self-tanning agent is, for example, dihydroxyacetone or erythrulose. Suitable tyrosine inhibitors, which prevent the formation of melanin and are used in depigmenting agents, are, for example, arbutin, ferulic acid, koji acid, coumaric acid and ascorbic acid (vitamin C). Suitable preservatives are, for example, phenoxyethanol, formaldehyde solution, parabens, pentanediol, chlorphenesin, caprylyl glycol, ethylhexylglycerine or sorbic acid and the silver complexes known under the name of Surfacine® and the other classes of compounds listed in Appendix 6, Parts A and B of the Kosmetikverordnung ("Cosmetics Directive"). Suitable perfume oils are mixtures of natural and synthetic perfumes. Natural perfumes are extracts of flowers, stems and leaves, fruits, fruit peel, roots, woods, herbs and grasses, needles and branches, resins and balsams. Also suitable are animal raw materials, for example civet and beaver, and synthetic perfume compounds of the ester, ether, aldehyde, ketone, alcohol and hydrocarbon type. Suitable pearlizing waxes or pearlizing agents, particularly for use in surfactant-containing formulations, are, for example, alkylene glycol esters, especially ethylene glycol distearate; stearyl citrate, cyclodextrine, fatty acid alkanolamides, especially cocofatty acid diethanolamide; partial glycerides, especially stearic acid monoglyceride; esters of polybasic, optionally hydroxy substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof. Superfatting agents may be selected from such substances as, for example, lanolin and lecithin and also polyethoxylated or acylated lanolin and -lecithin derivatives, polyol fatty acid esters, monoglycerides and fatty acid alkanolamides, the fatty acid alkanolamides also serving as foam stabilizers. Suitable superfatting agents are for example mixtures of coco-glucosides and glyceryl oleate (commercially available under the tradename Lamesoft® PO65). Metal salts of fatty acids such as, for example, magnesium, aluminium and/or zinc stearate or ricinoleate may be used as stabilizers.

Suitable fillers are substances which further improve for example the sensorical or cosmetic properties of a cosmetic composition and which, for example, provide or increase a velvety or silky skin feel (so called skin-sensory modifier). Suitable fillers according to the invention are starch and starch derivatives (such as e.g. tapioca starch, aluminium starch octenyl succinate, sodium starch octenyl succinate, distarch phosphate), pigments which do not mainly have UV-filter or colouring properties, such as e.g. Bornitrid) and/or Aerosil® (CAS-Nr. 7631-86-9), und/oder talkum, as well as Polymethyl Methacrylate (e.g. Cosmedia® PMMA V8/V12), Silica (e.g. Cosmedia® SILC), Stearalkonium Hectorite (as comprised in the commercially available product Cosmedia® Gel CC) as well as HDI/Trimethylol Hexyllactone Crosspolymer (as comprised in the commercially available product Cosmedia® CUSHION).

In addition, hydrotropes, for example ethanol, isopropyl alcohol or polyols, may be used to improve flow behavior. Suitable polyols preferably contain 2 to 15 carbon atoms and at least two hydroxyl groups. The polyols may contain other functional groups, more especially amino groups, or may be modified with nitrogen.

The compositions according to the invention and the esters according to the invention are suitable, particularly in cosmetic and/or pharmaceutical compositions, for wetting or impregnating or coating utility and hygiene wipes which are used for care and/or cleansing of the body. Examples of utility and hygiene wipes include tissues, papers, wipes, nonwovens, sponges, puffs, plasters and bandages which are used in the field of hygiene and care. These may be wet wipes for baby hygiene and baby care, cleaning wipes, facial wipes, skin care wipes, care wipes containing active ingredients against ageing of the skin, wipes containing sun protection formulations and insect repellents, wipes for decorative cosmetics or for after-sun treatment, toilet wipes, antiperspirant wipes, diapers, handkerchiefs, wet wipes, hygiene products and self-tanning wipes.

EXAMPLES

Example 1

1 mol of a mixture of n-octanoic acid and n-decanoic acid (60 weight-% of n-octanoic acid and 40 weight-% of decanoic acid) and 1.1 mol n-octanol as well as 0.22 g Fascat® 2001 (Sn oxalat) are combined and heated for 3 h at a temperature of 240° C. on a water separator. Then the product is distilled over a 30 cm column (153-168° C. at 0.8 mbar). The product is a colourless and odourless oil. It comprises 40 weight-% of an ester according to the general formula (I), wherein $R_1$ is a linear and saturated alkyl moiety with 9 carbon atoms.

Example 2

1 mol of a mixture of n-octanoic acid and n-decanoic acid (80 weight-% of n-octanoic acid and 20 weight-% of decanoic acid), 1.1 mol n-octanol as well as 0.22 g Fascat® 2001 (Sn oxalat) are combined and heated for 3 h at a temperature of 240° C. in a water separator. Then the product is distilled over a 30 cm column (153-168° C. at 0.8 mbar). The product is a colourless and odourless oil. It comprises 20 weight-% of an ester according to the general formula (I), wherein $R_1$ is a linear and saturated alkyl moiety with 9 carbon atoms.

Example 3

1 mol of a mixture of n-octanoic acid methyl ester and n-decanoic acid methyl ester (60 weight-% of n-octanoic acid methyl ester and 40 weight-% of decanoic acid methyl ester), 1.1 mol n-octanol as well as 0.22 g Fascat® 2001 (Sn oxalat) are combined and heated for 3 h at a temperature in the range of 180 to 220° C. on a water separator. Then the product is distilled over a 30 cm column (153-168° C. at 0.8 mbar). The product is a colourless and odourless oil. It comprises 40 weight-% of an ester according to the general formula (I), wherein $R_1$ is a linear and saturated alkyl moiety with 9 carbon atoms.

Example 4

1 mol of n-octanoic acid and 1.1 mol of a mixture of n-octanol and n-decanol (60 weight-% of n-octanol and 40 weight-% of n-decanol) as well as 0.22 g Fascat® 2001 (Sn oxalat) are combined and heated for 3 h at a temperature of 240° C. on a water separator. Then the product is distilled over a 30 cm column (153-168° C. at 0.8 mbar). The product is a colourless and odourless oil. It comprises 40 weight-% of an ester according to the general formula (I), wherein $R_2$ is a linear and saturated alkyl moiety with 10 carbon atoms.

In the following compositions, all numbers are weight.-% based on the final compositions.

TABLE 1

| | O/W Body Care Emulsions | | | | | | | | | | |
|---|---|---|---|---|---|---|---|---|---|---|---|
| Ingredients | 1 C | 2 C | 3 C | 4 L | 5 C | 6 L | 7 L | 8 C | 9 L | 10 C | 11 C |
| Eumulgin ® VL 75 | | | | | | | | 2.0 | | 1.5 | |
| Dehymuls ® PGPH | | 0.6 | | | | | | | | | |
| Generol ® R | | | 0.5 | | | | | | | | |
| Eumulgin ® B2 | | | 2.0 | | | | | | 2.0 | | |
| Tween ® 60 | | | | 0.2 | | | | | | | |
| Cutina ® E 24 | | | | | 0.2 | | | | | | |
| Hostaphat ® KL 340 N | | | | | | | | | 0.5 | | |
| Lanette ® E | | | | | | | | 0.6 | | | |
| Amphisol ® K | 0.2 | | | | | | | | | | |
| Sodium Stearate | | | | | | 0.5 | | | | | |

TABLE 1-continued

O/W Body Care Emulsions

| Ingredients | 1 C | 2 C | 3 C | 4 L | 5 C | 6 L | 7 L | 8 C | 9 L | 10 C | 11 C |
|---|---|---|---|---|---|---|---|---|---|---|---|
| Emulgade ® PL 68/50 | 3.0 | | | | | | 2.0 | | | | 1.2 |
| Eumulgin ® SG | 0.2 | | | | 0.2 | 0.3 | | | | | |
| Eumulgin ® Prisma | | 0.2 | | | | | 0.2 | | | 0.2 | 0.5 |
| Inwitor 372 P | | | | | | 3.0 | | | | 3.0 | |
| Tego ® Care CG | 0.7 | | | | | | | | | | |
| Tego ® Care 450 | | | | | 3 | | 1.0 | | | 1.0 | |
| Cutina ® PES | 2.5 | 2 | 3 | | | 2 | | 1.7 | 2.5 | | 1.2 |
| Cutina ® MD | | | 1 | 3 | 5 | | 2 | | | 3 | |
| Lanette ® 14 | | | | 1 | | | | 4 | | | 4 |
| Lanette ® O | 4.5 | | 4 | | 1 | | | | | | 2 |
| Novata ® AB | | 1 | | | | | | | | | 1 |
| Emery ® 1780 | | | | | 0.5 | 0.5 | | | | | |
| Lanolin, water-free, USP | | | | | | | 1.1 | | | | |
| Cosmedia ® DC | | 1.5 | 2 | | | 1.5 | 2 | | 1.5 | 1.5 | |
| Cetiol ® SB 45 | | | 1.5 | | | | 2 | | | | |
| Cegesoft ® C 17 | | | | | | | | | | | 2 |
| Myritol ® PC | | | | | 5 | | | | | | |
| Myritol ® 331 | 2 | 5 | 1 | | | 6 | | 6 | | | |
| Finsolv ® TN | | | 2 | | | 2 | | | | | |
| Ester mixture of example 1 | 4 | 3 | 4 | 5 | 4 | 4 | 4 | 6 | 8 | 3 | 5 |
| Cetiol ® Sensoft | 2.0 | | | | | 2.0 | | | | 3.0 | |
| Cetiol ® CC | | | 3 | | | | 4 | | | | 5 |
| Cetiol ® OE | | | 2.0 | | | | | | | 4 | |
| Dow Corning DC ® 245 | | | 2 | | 1 | 1 | | | | | |
| Dow Corning DC ® 2502 | | | | | 2 | 1 | | | | | |
| Prisorine ® 3758 | | | | | | 1 | | | | | |
| Silicone Oil Wacker AK ® 350 | 0.5 | 0.5 | 0.5 | | | 1 | | | | | |
| Cetiol ® 868 | | | | | 2 | 4 | | | | | |
| Cetiol ® J 600 | 2 | | 3 | | 3 | 2 | | | | 5 | |
| Ceraphyl ® 45 | | | | | | | 3 | | | | |
| Mineral Oil | | | | 9 | | | | | | | |
| Cetiol ® SN | | | 5 | | | | | | | | |
| Cetiol ® B | | | | | | | | 4 | | 2 | |
| Eutanol ® G | | 2 | | 3 | | | | | | | |
| Cetiol ® PGL | | | | | | | | | 5 | 5 | |
| Dry Flo ® Plus | 5 | | | | | | 1 | | | | |
| SFE 839 | 5 | | | | | | | | | | 2 |
| Almond Oil | | | | | | | 1 | | | | |
| Insect Repellent ® 3535 | | 2 | 4 | | | 2 | | | | 3 | |
| N,N-Diethyl-m-toluamide | | 2 | | | | | | | | 3 | |
| Photonyl ® LS | 2 | 2 | | | | 2 | | | | | |
| Panthenol | | | | | | | 1 | | | | |
| Bisabolol | | | | | | | 0.2 | | | | |
| Tocopherol/Tocopheryl Acetate | | | | | | | 1 | | | | |
| Veegum ® Ultra | | | | | | | | | | 1 | |
| Keltrol ® T | | | | 0.4 | | | | | | 0.5 | |
| Cosmedia ® SP | | 0.3 | | 0.2 | 0.2 | | | | | 0.2 | 0.3 |
| Pemulen ® TR 2 | 0.3 | | | | | | | | 0.3 | | |
| Carbopol ® Ultrez 10 | | | | | | 0.2 | | | | | |
| Rheocare ® C Plus | | | 0.3 | | 0.2 | | | | | | |
| Ultragel ™ 300 | | | | | | | | | | 0.2 | |
| Ethanol | | | | | | | | | | 10 | |
| Butylene glycol | | | | 4 | 3 | | 2 | 5 | 2 | | |
| Glycerin | 2 | 5 | 5 | | 3 | 3 | 2 | | 4 | | 3 |
| Water, Preservatives, NaOH | ad 100, q.s., pH 6.5-7.5 | | | | | | | | | | |

C—Cream, L—Lotion

TABLE 2

O/W Body Care Emulsions

| Ingredients | 12 C | 13 C | 14 L | 15 C | 16 L | 17 C | 18 C | 19 L | 20 L | 21 L | 22 C |
|---|---|---|---|---|---|---|---|---|---|---|---|
| Eumulgin ® VL 75 | | | 1 | | | | | | | | 1 |
| Generol ® R | | | | | | 0.3 | | | | | |
| Eumulgin ® B2 | | | | | | | | | | 2 | |
| Tween ® 60 | | | | 2 | | | | | | 1 | |
| Cutina ® E 24 | | | | 0.5 | | | | | | 1 | |
| Lanette ® E | 0.5 | | | | | | | | | | |
| Amphisol ® K | | 0.5 | | | | | | | 0.1 | | |
| Sodium Stearate | | | | | 1 | | | | | | |

TABLE 2-continued

O/W Body Care Emulsions

| Ingredients | 12 C | 13 C | 14 L | 15 C | 16 L | 17 C | 18 C | 19 L | 20 L | 21 L | 22 C |
|---|---|---|---|---|---|---|---|---|---|---|---|
| Emulgade ® PL 68/50 |  | 3 |  |  | 3.0 |  | 1 | 2 |  |  |  |
| Eumulgin ® SG |  |  |  |  |  | 0.5 |  |  |  | 0.5 |  |
| Eumulgin ® Prisma |  |  | 0.5 |  | 0.2 |  | 0.2 |  |  |  |  |
| Inwitor 372 P | 3 | 2 | 3 |  | 3 |  | 1 | 1 |  |  |  |
| Tego ® Care 450 |  |  |  | 1 |  | 2.0 | 3.8 | 1 | 1 |  |  |
| Cutina ® PES | 2 |  | 1 |  | 2.5 | 2 |  | 1.2 |  | 1.5 | 3 |
| Cutina ® MD | 3 | 1 |  | 4 |  |  |  | 2 |  | 1 |  |
| Lanette ® 14 |  | 2 |  |  | 1 |  | 2 |  |  |  |  |
| Lanette ® O | 2 |  |  | 2 |  | 3 | 1 |  | 1 | 1 | 6 |
| Novata ® AB |  |  |  |  |  |  |  |  | 1 | 1 |  |
| Emery ® 1780 |  |  |  |  |  |  |  |  |  |  | 0.5 |
| Lanolin, water-free, USP |  |  |  |  | 4 |  |  |  |  |  |  |
| Cosmedia ® DC |  |  | 1 |  | 1.5 |  |  |  | 1 | 1 |  |
| Cetiol ® SB 45 |  |  |  |  |  | 2 |  |  |  |  |  |
| Cegesoft ® C 17 | 4 |  |  |  |  |  |  |  |  |  |  |
| Myritol ® PC | 6 |  |  |  | 5 |  |  |  | 5 |  |  |
| Myritol ® 331 |  |  | 5 |  |  | 7 |  |  |  | 10 | 3 |
| Finsolv ® TN |  | 5 |  | 4 | 5 |  |  |  |  |  | 1 |
| Ester mixture of example 1 | 5 | 2 | 4 | 6 | 2 | 5 | 4 | 3 | 3 | 8 | 2 |
| Cetiol ® Sensoft |  | 2 | 3 |  |  |  |  |  |  |  |  |
| Cetiol ® CC |  |  | 4 |  |  |  | 3 |  |  |  |  |
| Cetiol ® OE | 2.5 |  |  |  |  | 2 |  | 5 |  |  |  |
| Dow Corning DC ® 245 |  |  |  | 1 |  | 3 |  |  |  |  | 2 |
| Dow Corning DC ® 2502 |  | 1 |  | 1 |  |  |  |  |  |  | 3 |
| Prisorine ® 3758 | 3 |  |  |  |  |  |  |  |  |  | 2 |
| Silicone Oil Wacker AK ® 350 |  |  |  | 1 |  |  |  |  |  |  | 1 |
| Cetiol ® 868 |  | 2 |  |  |  |  |  |  |  |  |  |
| Cetiol ® J 600 |  | 2 | 2 |  |  |  |  |  |  |  |  |
| Ceraphyl ® 45 |  |  |  |  |  | 3 |  |  |  |  |  |
| Cetiol ® SN |  |  | 5 |  |  |  |  |  |  |  |  |
| Cetiol ® B |  |  |  |  | 5 | 4 |  |  |  |  | 3 |
| Eutanol ® G |  | 3 | 5 |  |  |  |  |  |  |  |  |
| Cetiol ® PGL |  |  |  |  |  |  |  | 5 | 2 |  |  |
| Dry Flo ® Plus |  | 1 |  |  |  |  |  |  |  |  | 1 |
| SFE 839 | 1 | 1 |  |  |  |  |  |  |  |  |  |
| Almond Oil |  |  |  |  | 2 |  |  |  |  |  |  |
| Photonyl ® LS |  |  |  |  | 2 |  |  |  |  |  |  |
| Panthenol |  |  |  |  |  | 1 |  |  |  |  |  |
| Bisabolol |  |  |  |  |  | 0.2 |  |  |  |  |  |
| Tocopherol/Tocopheryl Acetate |  |  |  |  | 1 |  |  |  |  |  |  |
| Veegum ® Ultra |  |  |  |  |  |  |  | 1 |  |  |  |
| Keltrol ® T |  |  |  |  |  |  |  | 0.5 |  |  |  |
| Cosmedia ® SP | 0.1 | 1 |  | 0.2 | 0.2 | 0.2 | 0.2 |  |  |  | 0.5 |
| Carbopol ® ETD 2001 |  |  | 0.3 |  |  |  |  |  |  |  |  |
| Pemulen ® TR 2 |  |  |  |  | 0.3 |  |  |  |  |  |  |
| Rheocare ® C Plus | 0.2 | 0.3 |  |  |  |  |  |  |  |  |  |
| Ultragel ™ 300 |  |  |  | 0.4 |  | 0.3 |  |  |  | 0.4 |  |
| Ethanol |  | 5 |  | 8 |  |  |  |  |  |  | 10 |
| Butylene glycol | 5 |  |  | 3 | 3 |  |  |  |  | 8 |  |
| Glycerin | 2 | 4 | 3 | 3 |  | 7 | 5 | 3 | 5 |  |  |
| Water, Preservatives, NaOH | ad 100, q.s., (pH 6.5-7.5) | | | | | | | | | | |

C—Cream, L—Lotion

TABLE 3

O/W Body Care Emulsions

| Ingredients | 23 SC | 24 C | 25 C | 26 L | 27 C |
|---|---|---|---|---|---|
| Dehyquart ® C 4046 | 6 |  |  | 3 |  |
| Cutina ® GMS-SE |  |  |  |  | 5.5 |
| Cutina ® FS 45 |  |  |  |  | 1.5 |
| Eumulgin ® B2 |  | 1 |  |  |  |
| Eumulgin ® SG |  |  | 0.2 |  |  |
| Eumulgin ® Prisma |  | 0.2 |  |  |  |
| Inwitor 372 P |  |  | 2 |  |  |
| Cutina ® PES | 3 | 2 | 2 | 2 | 2 |
| Cutina ® MD |  | 1.5 |  |  |  |
| Cosmedia ® DC |  |  |  | 0.5 |  |
| Cegesoft ® PS 6 |  |  |  | 4.5 |  |
| Cegesoft ® SH |  | 7 | 3 |  |  |
| Myritol ® 331 |  |  | 5 | 4.5 |  |
| Ester mixture of example 1 | 4 | 5 | 4 | 3 | 4 |
| Cetiol ® Sensoft |  | 2 |  |  |  |
| Cetiol ® CC |  |  | 3 |  |  |
| Cetiol ® OE |  | 1 |  |  |  |
| Silicone Oil Wacker AK ® 350 |  |  |  |  | 0.5 |
| Paraffin Liquid |  |  |  |  | 2 |
| Isopropyl Palmitate |  |  |  | 2 |  |

TABLE 3-continued

O/W Body Care Emulsions

| Ingredients | 23 SC | 24 C | 25 C | 26 L | 27 C |
|---|---|---|---|---|---|
| Cetiol ® 868 | | 2 | 4 | | |
| Cetiol ® SN | 4 | | | | 3 |
| Eutanol ® G | | | | | 3 |
| Almond Oil | | | 7 | | |
| Panthenol | 1 | 0.2 | | 1 | |
| Bisabolol | | | | 1 | |
| Tocopherol/Tocopheryl Acetate | | | 0.2 | | |
| Keltrol ® T | | | | 1 | |
| Ultragel ™ 300 | 0.1 | | | 0.45 | |
| Cosmedia ® SP | | | 1 | 0.7 | |
| Glycerin | 2 | 5 | 5 | 5 | |
| Water, Preservatives, NaOH | | | ad 100, q.s. | | |

C—Cream, L—Lotion, SC = Sprayable Cream

TABLE 4

W/O Body Care Emulsions

| Ingredients (INCI) | 1 C | 2 L | 3 C | 4 L | 5 C | 6 L | 7 L | 8 L | 9 C | 10 C | 11 C |
|---|---|---|---|---|---|---|---|---|---|---|---|
| Dehymuls ® PGPH | 1 | 2 | 1 | 2 | 3 | 1 | 1 | 2 | | | 1 |
| Monomuls ® 90-O18 | 2 | | | | | | | | | 2 | 2 |
| Lameform ® TGI | 4 | 1 | | | 3 | | | 1 | 4 | 3 | |
| Abil ® EM 90 | | | | | | | 4 | | 1 | | |
| Isolan GPS | | | 2 | | 2 | | | | | 1 | |
| Isolan ® PDI | | | | | | | 4 | | | | 1 |
| Glucate ® DO | | | | 3 | | | | | | | |
| Arlacel ® 83 | | | 4 | | | | | | | | |
| Dehymuls ® LE | | 1 | 1 | 2 | | | | | | 1 | 1 |
| Dehymuls ® HRE 7 | | | | | | | | 4 | | 1 | |
| Zinc Stearate | 2 | 1 | | 1 | 1 | | | 1 | 1 | 1 | |
| Microcristalline Wax | | | 5 | | | 2 | | | | | 5 |
| Bees wax | 4 | | | 1 | | | | 1 | 4 | 7 | |
| Tego Care ® CG | | | | | 1 | | | | | | 0.5 |
| Prisorine ® 3505 | | | 1 | 1 | | 1 | 1 | | | | 1 |
| SFE ® 839 | | | | | | | 3 | | | | |
| Emery ® 1780 | 1 | | | | | | | | | | 1 |
| Anhydrous Lanolin USP | | | | 5 | | | | | | 4 | |
| Ester mixture of example 1 | 3 | 4 | 2 | 6 | 6 | 2 | | 2 | 6 | 3 | 8 | 1 |
| Cegesoft ® C 17 | | | 3 | | | | | | | 1 | |
| Myritol ® PC | | | | | | 2 | 4 | | | | |
| Myritol ® 331 | 6 | | | | 2 | 6 | 2 | | | | 8 |
| Finsolv ® TN | | | | 5 | | 2 | 5 | | | | |
| Cetiol ® A | | 6 | | | | 4 | | | | | |
| Cetiol ® Sensoft | | | | | 6 | 4 | | | | 4 | |
| Cetiol ® CC | | 8 | | | 2 | 2 | 2 | | | | 5 |
| Cetiol ® SN | | | 5 | | | | | 3 | | | |
| Cetiol ® OE | 3 | | | | 4 | | 2 | | 4 | 2 | |
| Dow Corning DC ® 244 | | | | | 1 | | 2 | | | | |
| Dow Corning DC ® 2502 | | | | 1 | 2 | | | | | | |
| Prisorine ® 3758 | | | | | 3 | | | | | | |
| Silicon Oil Wacker AK ® 350 | | | | 4 | | | 3 | | | | |
| Cetiol ® 868 | | | | | | | | | | 2 | 7 |
| Cetiol ® J 600 | | | 4 | | 2 | | | | | | |
| Ceraphyl ® 45 | | | | 2 | | | | 2 | | 6 | |
| Mineral oil | | | | | 4 | | | | | | |
| Cetiol ® B | | | | 2 | 4 | | | | | 3 | |
| Eutanol ® G 16 | | 1 | | | | | | | | 3 | |
| Eutanol ® G | | | | 3 | | | | 8 | | | |
| Cetiol ® PGL | | | | | | 4 | | | 9 | | |
| Almond Oil | | | | | 1 | 5 | | | | | |
| Insect Repellent ® 3535 | 2 | | | | | | | | | | |
| Unirep ® U-18 | | | | 3 | | | 5 | | | | |
| Photonyl ® LS | 2 | 2 | | | | | | | | | |
| Panthenol | | | | | | 1.0 | | | | | |
| Bisabolol | | | | | | 0.2 | | | | | |
| Copherol ® 1250 C | | | | | | 1 | | | | | |
| MgSO$_4$ × 7 H$_2$O | | | | | | 1 | | | | | |
| Bentone ® 38 | | | | | 1 | | | | | | |
| Propylene Carbonate | | | | | 0.5 | | | | | | |
| Ethanol | | | | | | | | | | 8 | |
| Butylene Glycol | | | 2 | 6 | | | 2 | 5 | | | 2 |
| Glycerin | 5 | 3 | 3 | | 5 | 3 | 2 | | 10 | 4 | |
| Water, Preservative | | | | ad 100, q.s. | | | | | | | |

L = Lotion, C = Cream

TABLE 5

| Ingredients | 1 L | 2 C | 3 S | 4 L | 5 C | 6 L | 7 L | 8 C | 9 L | 10 C | 11 L |
|---|---|---|---|---|---|---|---|---|---|---|---|
| O/W Sun Care Emulsions | | | | | | | | | | | |
| Eumulgin ® VL 75 | 2.0 | | | | | | | 2 | | | 2 |
| Eumulgin ® B2 | | | | 0.5 | | | | | | | |
| Tween ® 60 | | | | 0.2 | | | | | | | |
| Myrj ® 51 | | | | 0.5 | | | | | | | |
| Cutina ® E 24 | | | | 0.1 | | | | | | | |
| Hostaphat ® KL 340 N | | | | | | | | | 1.6 | | |
| Lanette ® E | | | 0.3 | | | | | | | | |
| Amphisol ® K | | | | | | | | | | 1 | |
| Sodium Stearate | | | | | | 1 | | | | | |
| Emulgade ® PL 68/50 | | 2 | 1 | | | 2 | 2 | | | 2 | |
| Imwitor 372 P | | 2 | | | | 1 | | 2 | | | |
| Eumulgin ® SG | | 0.5 | | | | 0.1 | | 0.2 | | | |
| Eumulgin ® Prisma | 0.1 | | | | 0.75 | | | | | | |
| Tego ® Care 450 | | | | | | 2 | | | | 1 | 2.5 |
| Cutina ® PES | 2 | | 2.5 | 1 | 2.5 | | 2.5 | | 2.5 | 1.7 | 1.5 |
| Cutina ® MD | 2 | | 1 | 2 | | | 2 | | | 6 | |
| Lanette ® 14 | 1 | | | 1 | | | | 2 | | | 2 |
| Lanette ® O | 1 | 6 | | | 5 | 2 | | 2 | | | |
| Cosmedia ® DC | 1 | 1.5 | | 1 | 1 | | 2 | 2 | | | 2 |
| Antaron ® V 216 | | | 2 | | | 1.5 | | | 1 | 1 | |
| Emery 1780 | | | | | 0.5 | 0.5 | | | | | |
| Lanolin, water-free USP | | | | | | | 5 | | | | |
| Myritol ® PC | | | | | 5 | | | | | | |
| Myritol ® 331 | | | 8 | | | 6 | | 10 | | 2 | |
| Finsolv ® TN | | | 1 | | | | | 1 | | | |
| Ester mixture of example 1 | 5 | 2 | 3 | 5 | 3 | 4 | 3 | 2 | 5 | 2 | 5 |
| Cetiol ® Sensoft | | 2.5 | | | 2 | | | | 3 | | |
| Cetiol ® CC | | | 2 | | | | 1 | | | | |
| Cetiol ® OE | | | 3 | | | | | | 2 | 3 | |
| Dow Corning DC ® 244 | 4 | | 1 | | | | | 2 | | | 2 |
| Dow Corning DC ® 2502 | | 1 | | | 2 | | | | | | |
| Squatol ® S | | | | | | | 4 | | | | |
| Silicone Oil Wacker AK ® 350 | | 2 | | | | | | | | | |
| Cetiol ® 868 | | | | | 2 | | 4 | | | | 2 |
| Cetiol ® J 600 | | | | | 3 | 2 | | | | 5 | |
| Mineral Oil | | | | 4 | | | | | | | |
| Cetiol ® B | | | 1 | | | | | | | 2 | |
| Eutanol ® G | | | | | 2 | | | | 4 | | |
| Eutanol ® G 16 | 4 | | | | | 4 | | | | | |
| Cetiol ® PGL | | 5 | | | | | | | | 5 | |
| Almond Oil | | | 2 | | | | 1 | | | | |
| Photonyl ® LS | | | | | 2 | | | | | 2 | |
| Panthenol | | | | | | 1 | | | | | |
| Bisabolol | | | | | | 0.2 | | | | | |
| Tocopherol/Tocopheryl Acetate | | | | | | 1 | | | | | |
| Photonyl ® LS | | | | | | | | | | | |
| Neo Heliopan ® AP (Na-salt) | | 1 | | | | | | | 1 | | |
| Neo Heliopan ® Hydro (Na-salt) | 2 | | 2.2 | | | | | | 1 | | |
| Neo Heliopan ® 303 | 3 | 5 | 9 | 4 | | | | | | | |
| Neo Heliopan ® BB | | | | | 1 | | | | | | 2 |
| Neo Heliopan ® MBC | 2 | | | 3 | | 2 | 2 | 2 | | | 1 |
| Neo Heliopan ® OS | | | | | | | | | 10 | 7 | |
| Neo Heliopan ® E 1000 | | 7.5 | | 6 | | | | | | | 6 |
| Neo Heliopan ® AV | | | 7.5 | | | 7.5 | 4 | 5 | | | |
| Uvinul ® A Plus | | | | 2 | 1 | | | | | | |
| Uvinul ® T 150 | 2 | | | | 2.5 | | | 1 | | | |
| Tinosorb ® M | | | 3 | | | | 2 | | | | 3 |
| Tinosorb ® S | | | 1 | | | | 1.5 | | | | |
| Uvasorb ® HEB | | 1 | | | 1 | | | | | | |
| Parsol ® 1789 | | 1 | 1 | | | 2 | | 2 | 2 | | |
| Zinkoxid NDM | 10 | | 5 | | | 10 | | 3 | | 5 | 4 |
| Eusolex ® T 2000 | | | | | 5 | | 3 | 3 | | | 4 |
| Veegum ® Ultra | 1.5 | | 0.75 | | | | | | 1 | 1 | |
| Keltrol ® T | 0.5 | | 0.25 | | | | | | 0.5 | 0.5 | |
| Cosmedia ® SP | 0.1 | 0.5 | | | 0.5 | | 0.2 | 0.2 | | 0.2 | 0.2 |
| Ultragel ™ 300 | | | | 0.2 | | 0.2 | | | 0.1 | | |
| Rheocare ® C plus | | | | | | | | | | 0.3 | 0.2 |
| Ethanol | | | | | | | | | | 10 | |
| Butylene glycol | | 2 | | 4 | 3 | | 2 | 5 | 2 | | 2 |
| Glycerin | 5 | 5 | 5 | | 3 | 3 | 2 | | 4 | | 3 |
| Preservatives, NaOH, Water | | | | | q.s. ad 100 | | | | | | |

C—Cream, L—Lotion

TABLE 6

O/W Sun Care Emulsions

| Ingredients | 12 L | 13 C | 14 L | 15 C | 16 L | 17 C | 18 S | 19 C | 20 C | 21 L | 22 L |
|---|---|---|---|---|---|---|---|---|---|---|---|
| Eumulgin ® VL 75 | | | 4 | | 1.8 | | | | | | |
| Eumulgin ® B2 | | | | | | | | | | 0.2 | |
| Tween ® 60 | | | | | | | | | | 0.3 | |
| Cutina ® E 24 | | | | | | | | | | 0.5 | |
| Hostaphat ® KL 340 N | | | | | | | | | | | 0.5 |
| Imwitor 372 P | 2 | | | 2 | | | 2 | | 2.0 | | |
| Eumulgin ® SG | | | | 0.1 | | 0.2 | | | | | |
| Eumulgin ® Prisma | | 0.3 | 0.2 | | | | | | | | |
| Lanette ® E | | | | | | | | 0.1 | 0.5 | | |
| Amphisol ® K | 0.5 | | | | | | | 1 | | | |
| Sodium Stearate | | | | | 1 | | | | | | |
| Emulgade ® PL 68/50 | | 1.5 | | 2 | | 3 | | 2 | | | |
| Tego ® Care 450 | 1 | | | | | 2 | | 2 | 0.8 | | |
| Cutina ® PES | 2 | 2 | 2.5 | 1.5 | 2 | 2 | 2.5 | 3 | | 1.5 | 1.5 |
| Cutina ® MD | 1 | | | 4 | 1 | 3 | | | 5 | | 1 |
| Lanette ® 14 | | 2 | | | | | | | | 1 | |
| Lanette ® O | | 2 | | 2 | | | | 2 | 1 | 1 | |
| Allianz ® OPT | 1 | | | 1 | 1 | | | 2 | | | 2 |
| Cosmedia ® DC | | 1.5 | 2 | | | 1.5 | 2 | | 1.5 | 1.5 | |
| Emery ® 1780 | | | | 1 | 1 | | | | | | |
| Lanolin, water-free, USP | | | | | | 1 | 1 | | | | |
| Myritol ® PC | | | | | | | | | 3 | | |
| Myritol ® 331 | 12 | | 12 | | | 8 | 8 | | | 5 | 3 |
| Finsolv ® TN | | | | | 3 | | | 3 | | | |
| Ester mixture of example 1 | 4 | 2 | 3 | 5 | 3 | 2 | 4 | 3 | 2 | 5 | 3 |
| Cetiol ® Sensoft | | | 3 | | | 5 | | | | | 2 |
| Cetiol ® CC | 2 | | | | | 1 | | | | | |
| Cetiol ® OE | | | | | 2 | | | | | | 2 |
| Dow Corning DC ® 244 | | | | | 1 | | | | | | |
| Dow Corning DC ® 2502 | | 1 | | | | | | 3 | | | |
| Ceraphyl ® 45 | | | | | | | | | | 2 | 2 |
| Silicone oil Wacker AK ® 350 | | | | | 1 | | | | | | |
| Cetiol ® 868 | | 2 | | | | | | | | | |
| Cetiol ® J 600 | | 2 | | | | | | | | | |
| Mineral Oil | | | | 5 | | | | | | | |
| Cetiol ® B | 4 | | 4 | | | | | 4 | | | |
| Eutanol ® G | | 3 | | | | 3 | | | | | |
| Eutanol ® G 16 S | 10 | | | | | | | | | | |
| Cetiol ® PGL | | | | | | | | | 2 | | |
| Photonyl ® LS | | | | | | | | | | 2 | |
| Panthenol | | | | | | 1 | | | | | |
| Bisabolol | | | | | | 0.2 | | | | | |
| Tocopherol/Tocopheryl Acetate | | | | | | 1 | | | | | |
| Neo Heliopan ® Hydro (Na-salt) | | | | | | | | | 3 | | |
| Eusolex ® OCR | 6 | | 9 | | 5 | 7 | 9 | | 4 | | 7 |
| Neo Heliopan ® AP (Na-salt) | | | | 0.5 | | 1 | | | | | |
| Neo Heliopan ® BB | | | | | | | | 1 | 1 | | 1 |
| Neo Heliopan ® MBC | | 2 | | 1 | | | | 3 | 1 | | 3 |
| Neo Heliopan ® OS | 2 | | | | | | | | 7 | | |
| Neo Heliopan ® E1000 | | 4 | | | | | | 5 | | | |
| Neo Heliopan ® AV | | 4 | | 7.5 | 5 | | | 5 | 4 | 7.5 | |
| Uvinul ® A PLUS | | | | | 1 | | 2 | | | | |
| Uvinul ® T 150 | 1 | | | | | | | | 1.3 | 1 | 1 |
| Tinosorb ® M | | | 6.5 | | | | | | 4 | | |
| Tinosorb ® S | | | 1 | | 2 | | | | | | |
| Uvasorb ® HEB | 1 | | | | | | | | | | 2 |
| Parsol ® 1789 | 1 | | | | | | | | 2 | | 1 |
| Z-Cote ® HP 1 | 7 | 2 | 5 | | | 7 | 5 | | 6 | 2 | |
| Eusolex ® T 2000 | 5 | 2 | | | 10 | | 10 | | 2 | | |
| Veegum ® Ultra | 1.5 | | 1.5 | | | 1.5 | 1.2 | | 1 | | |
| Keltrol ® T | 0.5 | | 0.5 | | | 0.5 | 0.4 | | 0.5 | | |
| Cosmedia ® SP | | | 0.2 | | | | 0.1 | | | | |
| Pemulen ® TR 2 | | 0.3 | | 0.3 | | | | 0.2 | | | |
| Ultragel ™ 300 | | | | | | | | | | 0.2 | 0.3 |
| Rheocare ® C Plus | | | | 0.3 | | | 0.1 | | | | |
| Ethanol | | 5 | | 8 | | | | | | | |
| Butylene glycol | 1 | | | 3 | 3 | | | | | 8 | 1 |
| Glycerin | 2 | 4 | 3 | 3 | | 3 | 3 | 3 | 5 | | 3 |
| Water/Preservatives/NaOH | | | | ad 100/q.s./q.s | | | | | | | |

C—Cream, L—Lotion

TABLE 7

W/O Sun Care Emulsionen

| Ingredients | 23 C | 24 L | 25 C | 26 L | 27 C | 28 L | 29 L | 30 L | 31 L | 32 C | 34 C |
|---|---|---|---|---|---|---|---|---|---|---|---|
| Dehymuls ® PGPH | 4 | 3 | 1 | 3 | 2 | 1 | 1 | 1 | | | |
| Monomuls ® 90-O18 | | 1 | 2 | | | | | | 2 | 4 | |
| Lameform ® TGI | 2 | | | | 3 | | | | | 1 | 3 |
| Abil ® EM 90 | 2 | | | | | | 4 | | 1 | | 1 |
| Isolan GPS | | | 4 | | 3 | | | 2 | | | |
| Isolan ® PDI | | | | | | 4 | | 2 | | | |
| Zinc Stearate | 1 | | | 1 | 1 | | | 1 | | 1 | |
| Beeswax | 1 | | 5 | 1 | 3 | | | 2 | | 7 | 5 |
| Tego ® Care CG | | | | | 1 | | | | | | 0.5 |
| Cutina ® PES | | | 2 | | | 1 | 1 | | | | |
| Prisorine ® 3505 | | | 1 | | | 1 | 1 | | | | 1 |
| Cosmedia ® DC | 3 | 4 | 2 | 1 | 1 | 2 | 2 | 2 | 3 | 1 | 1 |
| Myritol ® 331 | 2 | | | | 3 | 3 | | | | | 8 |
| Finsolv ® TN | | | | 2 | | | | | | | |
| Ester mixture of example 1 | 5 | 4 | 2 | 3 | 4 | 3 | 5 | 5 | 4 | 4 | 5 |
| Cetiol ® Sensoft | | | | 3 | | | 5 | | | 3 | |
| Cetiol ® CC | 5 | | | | | 2 | | | 2 | 3 | |
| Tegosoft ® DEC | | 4 | | | 2 | | | | | | |
| Cetiol ® OE | | | | | 4 | | 5 | | | 2 | |
| Dow Corning ® DC 244 | | | 3 | | | | 2 | | 4 | | |
| Dow Corning ® DC 2502 | 1 | | 1 | | 2 | 1 | | | | | 1 |
| Silicone oil Wacker AK 350 | | 1 | | 4 | | | | 3 | | | |
| Cetiol ® PGL | | 3 | | | | 4 | | | 4 | | |
| Copherol ® F 1300 | | | | | | 1 | | | | | |
| MgSO$_4$ * 7H$_2$O | | | | | | 1 | | | | | |
| Neo Heliopan ® Hydro (Na-salt) | 2 | | 2.2 | | 3 | 3 | | | 1 | | 2 |
| Neo Heliopan ® 303 | | 5 | | | | | | | 4 | 4 | |
| Uvasorb ® HEB | 1 | | | 1 | 1 | | | | | | 2 |
| Neo Heliopan ® MBC | 2 | | | | | 2 | 2 | 2 | | | |
| Uvinul ® A Plus | | | | | 2 | | | | 3 | 3 | |
| Neo Heliopan ® AP (Na-salt) | | 2 | 2 | | 1 | | | | 1 | | 6 |
| Neo Heliopan ® AV | 3 | | 4 | 6 | 4 | 7.5 | 4 | 5 | | | 1 |
| Uvinul ® T 150 | 1 | 1 | | | 2.5 | | | 1 | | | |
| Parsol ® 1789 | 2 | 1 | | | | | 2 | | 2 | 2 | |
| Zinkoxid NDM | | | | | | 10 | | 3 | | | 4 |
| Tinosorb ® M | | 3 | | 3 | | | | 2 | | 2 | |
| Tinosorb ® S | | 3 | | 3 | | | | 2 | | 2 | |
| Eusolex ® T Aqua | | | 8 | | | | | 5 | | | |
| Eusolex ® T 2000 | | | | | 5 | | 3 | 3 | | | 4 |
| Ethanol | | | | | | | | | | 8 | |
| Glycerin | 5 | 3 | 3 | 3 | 5 | 3 | 2 | 3 | 10 | 4 | 3 |
| Water, Preservatives | | | | | ad 100, q.s. | | | | | | |

C—Cream, L—Lotion

TABLE 8

W/O Sun Care Emulsionen

| Ingredients | 12 | 13 | 14 | 15 | 16 | 17 |
|---|---|---|---|---|---|---|
| Dehymuls ® PGPH | 1 | 1 | | | 1 | 1 |
| Dehymuls ® LE | 1 | 2 | 1 | 1 | 1 | 1 |
| Abil ® EM 90 | | | | 4 | | |
| Isolan GPS | 3 | | | 1 | 1 | |
| Isolan ® PDI | | | | 4 | | 2 |
| Zinc Stearate | | | 1 | | | 1 |
| Beeswax | | | 1 | | | 5 |
| Cutina ® PES | | | 1 | | 1 | |
| Prisorine ® 3505 | | | | 1 | 1 | |
| Cosmedia ® DC | 4 | 1 | | 2 | 2 | 3 |
| Myritol ® 331 | | | | 3 | | |
| Finsolv ® TN | | | 2 | | | |
| Ester mixture of example 1 | 4 | 3 | 3 | 5 | 5 | 4 |
| Cetiol ® CC | | | | 2 | | 2 |
| Cetiol ® Sensoft | | 2 | | 2 | | 4 |
| Tegosoft ® DEC | 4 | 3 | | | 5 | |
| Cetiol ® OE | 2 | | | | 5 | |
| Dow Corning ® DC 244 | | | | | 2 | 4 |
| Dow Corning ® DC 2502 | | | 1 | | | |
| Silicone oil Wacker AK 350 | 1 | 4 | | | 3 | |
| Cetiol ® PGL | 3 | | | 4 | | 4 |
| Copherol ® F 1300 | | | | | 1 | |
| MgSO$_4$ * 7H$_2$O | | | | | 1 | |
| Neo Heliopan ® Hydro (Na-salt) | | | | 3 | | 1 |
| Neo Heliopan ® 303 | 5 | | | | | 4 |
| Uvasorb ® HEB | | | 1 | | | |
| Neo Heliopan ® MBC | | | | 2 | 2 | 2 |
| Uvinul ® A Plus | | | | | | 3 |
| Neo Heliopan ® AP (Na-salt) | 2 | | | | | 1 |
| Neo Heliopan ® AV | | | 6 | 7.5 | 4 | 5 |
| Uvinul ® T 150 | 1 | | | | 1 | |
| Parsol ® 1789 | 1 | | | 2 | | 2 |
| Zinkoxid NDM | | | | 10 | | 3 |
| Tinosorb ® M | 3 | 3 | | | | 2 |
| Tinosorb ® S | 3 | 3 | | | | 2 |
| Eusolex ® T Aqua | | | | | | 5 |
| Eusolex ® T 2000 | | | | | 3 | 3 |

TABLE 8-continued

W/O Sun Care Emulsionen

| Ingredients | 12 | 13 | 14 | 15 | 16 | 17 |
|---|---|---|---|---|---|---|
| Glycerin | 3 | 3 | 3 | 2 | 3 | 10 |
| Water, Preservatives | | | ad 100, q.s. | | | |

TABLE 9

Decorative Cosmetics - O/W Foundations

| Ingredients | 1 | 2 | 3 | 4 | 5 | 6 | 7 | 8 |
|---|---|---|---|---|---|---|---|---|
| Cutina ® GMS-SE | 5.5 | | | | | | | 3.0 |
| Emulgade ® PL 68/50 | | 5.0 | | | 2.0 | | | |
| Eumulgin ® VL 75 | | | 3.0 | | | 5.0 | | |
| Tego Care ® 450 | | | | | 2.0 | 2.0 | | |
| Codesta ® F-50 | | | | 6.0 | | | | |
| Amphisol ® K | | | 2.0 | | | | | |
| Lanette ® E | | 0.25 | | | | | | |
| Eumulgin ® SG | | | | | 1.0 | | 1 | |
| Eumulgin ® Prisma | | | | | | 1.0 | | 0.75 |
| Imwitor 372 P | | 2 | | | | | 1 | |
| Cutina ® FS 45 | 1.5 | | | | | | | |
| Eumulgin ® B 2 | | | 2.0 | | | | | |
| Cutina ® PES | 2.0 | 1.0 | 2.0 | 4.0 | 2.0 | 1.0 | 2.5 | 2.0 |
| Lanette ® O | | | 2.0 | | | | | 1.0 |
| Cutina ® MD | | 0.5 | 3.0 | 3.0 | | | | |
| Cetiol ® LC | 4.0 | | | | | | | |
| Cosmedia ® DC | 0.5 | | | 1.0 | | | | 1.0 |
| Ester mixture of example 1 | 4.0 | 5.0 | 4.0 | 2.0 | 7.0 | 5.0 | 10.0 | 4.0 |
| Cetiol ® Sensoft | 2.0 | | | | 3.0 | | | 2.0 |
| Tegosoft ® DEC | | 5.0 | | 2.0 | | 2.0 | | 2.0 |
| Cetiol ® CC | | | 2.0 | | 2.0 | | | |
| Dow Corning ® 245 | | 2.0 | | 2.0 | | | | |
| Eutanol ® G 16 | 4.0 | | | | | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | 2.0 | | | | | | 1.0 | 1.0 |
| Tinosorb ® M | | | 2.0 | | | | | 2.0 |
| Tinosorb ® S | | | | | 3.0 | | | 2.0 |
| Neo Heliopan ® AV | | | | | 2.0 | | 2.0 | |
| Heo Heliopan ® AP | | | | | 1.0 | | 1.0 | |
| Uvinul ® A Plus | | | 1 | | | | 2.0 | 2.0 |
| Microna ® Matte White | 5.0 | 5.0 | | | 5.0 | 5.0 | 5.0 | |
| Microna ® Matte Black | 0.3 | 0.3 | 0.1 | 0.3 | 0.3 | 0.3 | 0.4 | 0.3 |
| Microna ® Matte Yellow | 3.0 | 3.0 | | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® | 1.0 | 1.0 | | 1.0 | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | 5.0 | 5.0 | 5.0 | 3.0 | |
| Cosmedia ® SP | | | 0.3 | | 0.2 | | | |
| Water, de-ionized, Preservative | | | | ad 100 | | | | |

TABLE 10

Decorative Cosmetics - W/O Foundations

| Ingredients | 1 | 2 | 3 | 4 | 5 | 6 | 7 | 8 |
|---|---|---|---|---|---|---|---|---|
| Dehymuls ® PGPH | | 5.5 | | 4.0 | | | | 3.0 |
| Lameform ® TGI | | | 5.0 | | | 2.0 | | |
| Abil ® EM 90 | | | | | 3.0 | | 5.0 | |
| Isolan ® GI 34 | | | | | | | 2.0 | 2.0 |
| Isolan ® PDI | | | | 1.0 | 6.0 | | | |
| Isolan ® GPS | | 1.0 | 2.0 | | 1.0 | | | |
| Admul ® WOL 1403 | | | | 2.0 | | | | |
| Dehymuls ® HRE 7 | | | 1.0 | | | 1.0 | 1.0 | |
| Monomuls ® 90-O18 | | 1.5 | | | | | | 2.0 |
| Cutina ® PES | 2.0 | 1.0 | 2.0 | 4.0 | 2.0 | 1.0 | 2.5 | 2.0 |
| Cera Bellina | | | | 2.0 | | | | 2.0 |

TABLE 10-continued

Decorative Cosmetics - W/O Foundations

| Ingredients | 1 | 2 | 3 | 4 | 5 | 6 | 7 | 8 |
|---|---|---|---|---|---|---|---|---|
| Beeswax | | 2.0 | | | 2.0 | | | 1.0 |
| Microcrystalline Wax | | | 1.5 | 3.0 | 3.0 | | | |
| Cetiol ® LC | 4.0 | 5.0 | | | | | | |
| Cosmedia ® DC | 1.0 | | | | 0.5 | | 1.0 | |
| Ester mixture of example 1 | 4.0 | 2.0 | 2.0 | 4.0 | 5.0 | 5.0 | 5.0 | 4.0 |
| Cetiol ® Sensoft | | 2.0 | | | 2.0 | | 5.0 | |
| Tegosoft ® DEC | | 3.0 | | | | 2.0 | | |
| Cetiol ® CC | | | | | 2.0 | | | 2.0 |
| Dow Corning ® 245 | | 2.0 | | 2.0 | | | | 2.0 |
| Eutanol ® G 16 | 4.0 | | | | 3.0 | 3.0 | | |
| Myritol ® 331 | | 5.0 | | | 2.0 | 2.0 | 5.0 | |
| Uvinul ® T 150 | | | | 0.5 | | | | 0.5 |
| Uvasorb ® HEB | | 2.0 | | | | | 1.0 | 1.0 |
| Tinosorb ® M | | 2.0 | | | | | | 2.0 |
| Tinosorb S | | | | 3.0 | | | | 2.0 |
| Neo Heliopan ® AV | | | | | 2.0 | | 2.0 | |
| Heo Heliopan ® AP | | | | | 1.0 | | 1.0 | |
| Uvinul ® A plus | | | 1.0 | | | | 2.0 | 2.0 |
| Microna ® Matte White | 5.0 | 5.0 | | 5.0 | 5.0 | 5.0 | | 5.0 |
| Microna ® Matte Black | 0.3 | 0.3 | 0.1 | 0.3 | 0.3 | 0.3 | 0.4 | 0.3 |
| Microna ® Matte Yellow | 3.0 | 3.0 | 3.5 | 3.0 | 3.0 | 3.0 | 2.0 | 3.0 |
| Microna ® Matte Red | 0.6 | 0.6 | 1.0 | 0.6 | 0.6 | 0.6 | 1.0 | 0.6 |
| Ronasphere ® | 1.0 | 1.0 | | 1.0 | 1.0 | 1.0 | | 1.0 |
| Pigment White 6 | | | 6.0 | | | | 6.0 | |
| Dry Flow PC | | | | | | | 2.0 | 2.0 |
| Glycerin | 5.0 | 5.0 | 3.0 | 5.0 | 5.0 | 5.0 | 3.0 | |
| Water, de-ionized, Preservative | | | | ad 100 | | | | |

TABLE 11

Decorative Cosmetics - Lipsticks

| Ingredients | 1 | 2 | 3 | 4 |
|---|---|---|---|---|
| Cutina ® LM conc | | | 10.0 | 36.0 |
| Candelilla Wax | 9.39 | 5.0 | 10.0 | |
| Carnauba wax | 2.85 | 7.0 | 5.0 | |
| Beeswax | 1.86 | 5.0 | 4.0 | |
| Cutina ® PES | 3.2 | 5.0 | 6.4 | 4.5 |
| Cetiol ® MM | | | 5.0 | |
| Cosmedia ® DC | 5.0 | 4.0 | 2.0 | 6.0 |
| Ester mixture of example 1 | 7.0 | 6.0 | 3.0 | 5.0 |
| Cetiol ® Sensoft | 2.0 | | 4.5 | |
| Tegosoft ® DEC | 3.0 | 3.0 | 3.0 | 5.0 |
| Eutanol ® G | 10.97 | 12.0 | 12.0 | |
| Fitoderm ® | | | | 4.0 |
| Monomuls ® 90L 12 | | | 3.0 | |
| Dehymuls ® PGPH | | | 4.0 | |
| Castor Oil | 11.0 | 15.5 | 14.5 | 30.0 |
| Copherol ® F 1300 | 1.0 | 1.0 | 1.0 | 1.0 |
| Cosmetic white C47056 | 5.0 | 2.0 | 5.0 | |
| FDC Yellow 6 Al Lake C705270 | 7.0 | 7.0 | 8.0 | |
| DC Red 7 Ca Lake C 19003 | 6.0 | 4.5 | 1.1 | 2.9 |
| Irodin 100 Silverpearl | | | | 9.6 |
| Hydagen ® CMF | | 10.0 | | |
| Irwinol ® LS 9319 | 1.0 | | 3.0 | |
| Mineral Oil | 12.8 | | | |
| Petrolatum | 6.84 | 3.0 | | |
| Ceresin | 2.75 | | | |
| Microcrystalline Wax | 2.45 | | | |
| Colophane Claire type Y | 1.89 | | | |

TABLE 12

AP/Deo Concepts

| Ingredients (INCI) | 1 | 2 | 3 | 4 | 5 | 6 | 7 |
|---|---|---|---|---|---|---|---|
| Glyceryl Stearate, Ceteareth-20, Ceteareth-12, | 6 | | | 4.5 | | 6 | |

TABLE 12-continued

AP/Deo Concepts

| Ingredients (INCI) | 1 | 2 | 3 | 4 | 5 | 6 | 7 |
|---|---|---|---|---|---|---|---|
| Cetearyl Alcohol, Cetyl Palmitate (Emulgade ® SE) | | | | | | | |
| Ceteareth-20 (Eumulgin ®B2) | | | | 1 | | | |
| Glyceryl Stearate Citrate (Imwitor 372 P) | | 4.0 | | | | | |
| Polyglyceryl-3 Diisostearate (Lameform ® TGI) | | | 3 | | | | |
| Cocoglycerides (Novata ® AB) | | | | | | | 4 |
| Stearyl alcohol (Lanette ® 18) | | | | | 10 | | |
| Hydrogenated Castor Oil (Cutina ® HR) | | | | | 3.7 | | 6.5 |
| Polyglyceryl-2 Dipolyhydroxystearate (Dehymuls ® PGPH) | | | 1 | | | | |
| Sodium Stearoyl Glutamate (Eumulgin ® SG) | | 0.2 | | | | | |
| Disodium Cetearyl Sulfosuccinate (Eumulgin ® Prisma) | 0.3 | | | | | | |
| Sodium Cetearyl Sulfate (Lanette ® E) | | | | | 0.3 | | |
| Pentaerythrityl Distearate (Cutina ® PES) | 5 | 1 | 2 | 1 | 4.7 | 5 | 4 |
| Behenyl Alcohol (Lanette ® 22) | 2 | 1 | | | 4 | | |
| Ester mixture of example 1 | 4 | 4 | 5 | 3 | 4 | 3 | 5 |
| Propylheptyl Caprylate (Cetiol ® Sensoft) | | 2 | | | 20 | | 10 |
| Dicaprylyl Carbonate (Cetiol ® CC) | | | 2 | | | | |
| Dicaprylyl Ether (Cetiol ® OE) | 2 | | 2 | 5 | 3 | | 4 |
| Cocoglycerides (Myritol ® 331) | | | | | | | |
| Diethylhexyl-cyclohexane (Cetiol ® S) | | | | 5 | 14.7 | | 25 |
| Cyclopentasiloxane | 3 | | 5 | | 14 | 3 | 14 |
| Cyclopentasiloxane and Dimethicone/Vinyl-dimethicone Crosspolymer SFE 839 (GE Bayer) | | | 3 | | | | |
| Dimethicone AK 350 | 1 | 2 | | | | | |
| Hydrogenated Dimer Dilinoleyl/Dimethyl-carbonate Copolymer (Cosmedia ® DC) | 0.5 | | 1 | 1.5 | 1 | 2 | 1 |
| Triethyl Citrate (Hydagen ® C.A.T) | | | | 2 | | | |
| Tocopheryl Acetate | | | | | 1 | | |
| Aluminium Zirconium Tetrachloro-hydrex GLY (Rezal 36) | 30 | | 40 | | 22.9 | 30 | 25 |
| Aluminum Chlorhydrate (Locron L) | | 20 | | 10 | | | |
| Chitosan (Hydagen ® DCMF) | 0.05 | | | | | | |
| Glycolic Acid | 0.02 | | | | | | |
| Glycerin | | | 5 | 5 | | | |
| Propylene Carbonate (Fluka) | | | | | | | 0.5 |
| Quaternium-18 Hectorite (Bentone 18) | | | | | | | 1 |
| Polyquaternium-37 (Ultragel 37) | | 5 | | | | | |
| Talcum (Merck) | | | | | | 5 | 5 |
| MgSO₄ × 7H₂O | | | 1 | | | | |
| Water, Perfume, Preservatives | q.s. | q.s. | q.s. | q.s. | q.s. | q.s. | q.s. |

1/2—Antiperspirant/deo cream,
3—Antiperspirant cream (W/0),
4—Antiperspirant/deo spray,
5—Antiperspirant stick with vitamin E,
6—Antiperspirant cream,
7—Antiperspirant cream 'Soft Solid'

TABLE 13

Hair Care Conditioners

| | 1 | 2 | 3 | 5 | 6 | 7 | 8 |
|---|---|---|---|---|---|---|---|
| Structure ® XL (*) Hydroxypropyl Starch Phosphate | 5.0 | 5.0 | 5.0 | 4.0 | | | |
| Emulgade ® Sucro Sucrose Polystearate, Hydrogenated Polyisobutene | | | | | 1.0 | 1.0 | 1.0 |
| Dehyquart ® L 80 Dicocoylethyl Hydroxyethylmonium Methosulfate, Propylene Glycol | 2.6 | 1.3 | 2.0 | | | 0.5 | 0.5 |
| Dehyquart ® F 75 Distearoylethyl Hydroxyethylmonium Methosulfate, Cetearyl Alcohol | | | | 2.0 | | | |
| Dehyquart ® C 304 Aqua, Cocamidopropyl-trimonium Methosulfate, Propylene Glycol | | | | 3.7 | | 4.0 | 4.0 |

TABLE 13-continued

Hair Care Conditioners

| | 1 | 2 | 3 | 5 | 6 | 7 | 8 |
|---|---|---|---|---|---|---|---|
| Ester mixture of example 1 | 1.0 | 3.0 | 1.0 | 0.5 | 2.0 | 1.5 | 1.5 |
| Dehyquart ® A CA Cetrimonium Chloride | | | | | 4.0 | | |
| DC 200 (***) Dimethicone | | | | 0.5 | | | |
| Lanette ® O Cetearyl Alcohol | | | 1.0 | | 4.0 | | |
| Lamesoft ® TM Benz Glycol Distearate, Coco Glucoside, Glyceryl Oleate, Glyceryl Stearate | 4.0 | | | 1.0 | | | |
| Gluadin ® WLM Hydrolyzed Wheat Protein | 1.0 | 1.0 | | 1.0 | | | 0.3 |
| Glycerin | | | 0.5 | | | | |
| Gluadin ® Soy Hydrolyzed Wheat Protein | | 0.5 | | | | | |
| Cacao Butter (**) *Theobroma Cacao* (Cocoa) Seed Butter | | | 0.5 | | | | |
| Herbalia ® Balm Mint *Melissa Officinalis*, Maltodextrin, Silica | | 0.01 | | | | | 0.02 |
| Ultragel ™ 300 Polyquarternium-37 | | | | | | 0.2 | 0.2 |
| Perfume, preservative | q.s. | q.s. | q.s. | q.s. | q.s. | q.s. | q.s. |
| Deionized water | Up to 100 | Up to 100 | Up to 100 | Up to 100 | Up to 100 | Up to 100 | Up to 100 |

(*) National Starch,
(**) Nederland,
(***) Dow Corning; pH adjusted to 3.5-5.0

TABLE 14

Hair Care Conditioners

| | 9 | 10 | 11 | 12 |
|---|---|---|---|---|
| Dehyquart ® L 80 Dicocoylethyl Hydroxyethylmonium Methosulfate, Propylene Glycol | 1.3 | 1.3 | | 1.0 |
| Dehyquart ® F 75 Distearoylethyl Hydroxyethylmonium Methosulfate, Cetearyl Alcohol | 1.3 | 1.3 | 1.3 | 1.5 |
| Lanette ® O (Cetearyl Alcohol) | 5.0 | 5.0 | 4.0 | 4.5 |
| Ester mixutre of example 1 | 1.0 | 1.0 | 1.0 | 0.5 |
| Cetiol ® SB 45 *Butyrospermum Parkii* (Shea Butter) | 4.0 | 4.0 | 2.0 | 4.5 |
| Gluadin ® Almound (Hydrolyzed Sweet Almound Protein) | | | 0.1 | 0.5 |
| ASCO BTAC (Behentrimonium Chloride) | | | 1.3 | |
| DC 949 (****)Amodimethicone, Trideceth-12, Cetrimonium Chloride | | | 1.0 | |
| Cegesoft ® PFO (*Passiflora Incarnata* Seed Oil) | | | | 2.0 |
| Aloveria ® (*Aloe Barbadensis*) | 0.1 | | | |
| Sphingoceryl ® Veg: Octyldodecanol, Hydrogenated Coco Glycerides, *Helianthus Annuus* (Sunflower) Seed Extract | 1.0 | | | |
| Copherol ® 1250 (Tocopheryl Acetate) | 0.2 | | | |
| Ultragel ™ 300 (Polyquarternium-37) | | 0.1 | | 0.2 |
| Perfume, preservative | q.s. | q.s. | q.s. | q.s. |
| Deionized water | Up to 100 | Up to 100 | Up to 100 | Up to 100 |

(****)Dow Corning; pH adjusted to 3.5-5.0

TABLE 15

Hair Care Conditioners

| | 13 | 14 | 15 | 16 |
|---|---|---|---|---|
| Ester mixture of example 1 | 10 | 10.6 | 43.6 | 30 |
| Myritol ® 318 (Caprylic Capric Triglyceride) | | | 43.6 | 20 |
| Cetiol ® ISL (Isostearyl Lactate) | | | | 40 |
| DC 1501 (*) (Cyclomethicone, Dimethiconol) | 69.5 | | | |
| Emery ® 3004 (Hydrogenated Polydecene) | | 67.8 | | |
| DC 345 (*) Cyclomethicone | 20 | | | |
| Versagel MC 750 (**) Isohexadecene, Ethylene/Propylene/Styrene Copolymer, Butylene/Ethylene/Styrene Copolymer | | 21.3 | | |
| DC 556 (*) Phenyl Trimethicone | 0.5 | | | |
| Wacker HDK H 20 (***): Phenyl Trimethicone | | | 12.5 | 10 |
| Ultragel ™ 300 (Polyquarternium-37) | 0.2 | | | 0.2 |
| Perfume | q.s. | q.s. | q.s. | q.s. |

(*) Dow Corning,
(**) Penreco,
(***) Wacker

TABLE 16

Hair Care Conditioners

| Ingredients (INCI) | 17 | 18 | 19 | 20 | 21 |
|---|---|---|---|---|---|
| Cetearyl Alcohol (Lanette ® O) | 5.0 | 4.5 | | | |
| Glyceryl Stearate (Cutina ® MD) | 4.0 | | | 14.5 | |
| Cetearyl Alcohol (Lanette ® O) | | | | 7.0 | |
| Hydrogenated Castor Oil (Cutina ® HR) | | | | 2.5 | |
| Cetyl Palmitate (Cutina ® CP) | | 0.3 | | 7.0 | |

TABLE 16-continued

Hair Care Conditioners

| Ingredients (INCI) | 17 | 18 | 19 | 20 | 21 |
|---|---|---|---|---|---|
| Paraffin Oil | | | | 23.5 | |
| Vaseline | | | | 32.5 | |
| Wacker Silicon Oil AK 350 | | | | 0.5 | |
| Ester mixture of example 1 | 3.0 | 0.2 | 1.5 | 2.0 | 5.0 |
| Oleyl Erucate (Cetiol ® J 600) | 2.0 | | | | |
| PEG-7 Glyceryl Cocoate (Cetiol ® HE) | | | | | 20.0 |
| Dimethicone (Dow Corning 200) | | 0.2 | | | |
| Ceteareth-12 (Eumulgin ® B1) | 1.0 | | | | |
| Ceteareth-20 (Eumulgin ® B2) | | 0.4 | | | |
| Ceteareth-30 (Eumulgin ® B3) | | | | | 14.0 |
| Cetoleth-20 (Eumulgin ® O20) | | | | 5.0 | |
| Glycerin, Glyceryl Polyacrylate (Hispagel ® 200) | | | 36.7 | | |
| Lauryl Glucoside (Plantacare ® 1200 UP) | | | | | 5.0 |
| Laureth-7 Citrate (Plantapon ® LC 7) | | | 0.7 | 1.0 | |
| *Glycine Soja* (Soybean) Sterols (Generol ® 122 N) | 0.5 | | | | |
| Hydrogenated Dimer Dilinoleyl/Dimethylcarbonate Copolymer (Cosmedia ® DC) | 1.0 | | | | |
| Glycerin | 3.0 | | | | |
| Cocamide MEA (Comperlan ® 100) | | | | | 2.5 |
| Cetrimonium Chloride (Dehyquart ® A) | 3.0 | 4.0 | | | |
| Hydrolyzed Keratin (Nutrilan ® Keratin W) | 2.0 | | | | |
| PVP/VA (Luviskol ® VA 64) | | | 4.5 | | |
| PEG-90M (Polyox ® WSR-301) | | | 0.25 | | |
| Hydroxypropyl Methylcellulose (Methocel ® E4M Premium EP) | | | 0.6 | | |
| Dicocoylethyl Hydroxyethylmonium Methosulfat, Propylene Glycol (Dehyquart ® L 80) | | | 0.6 | | |
| Triethanolamine | | | 1.0 | | |
| CaCl$_2$ * 2H$_2$O | | 0.1 | | | |
| Ethanol | | | 12.0 | | |
| Polyquarternium-37 (Ultragel ™ 300) | 0.2 | | | | |
| Water, Perfume, Preservatives | q.s. | q.s. | q.s. | q.s. | q.s. |

TABLE 17

Rinse-Off Concepts

| Ingredients (INCI) | 1 | 2 | 3 | 4 | 5 | 6 |
|---|---|---|---|---|---|---|
| Sodium Laureth Sulfate (Texapon ® N 70) | 12.9 | | 12.3 | 14.3 | 14.3 | |
| Cocamidopropyl Betaine (Dehyton ® PK 45) | 7.7 | | 5.4 | 5.4 | 5.4 | |
| Laureth-7 Citrate (Plantapon ® LC 7) | 10.0 | 2.5 | | | | 10.0 |
| Guar Hydroxypropyl-trimonium Chloride (Cosmedia ® Guar C 261N) | | | 0.25 | 0.2 | | |
| Polyquaternium-7 | | | | 2.5 | | |
| Polyquaternium-10 | | | | | 0.15 | |
| Polyquaternium-44 | | | 1.5 | | 1.5 | |
| Glycol Distearate, Laureth-4, Cocamidopropyl Betaine (Euperlane ® PK 4000) | | | 10.0 | 2.0 | 2.0 | |
| PEG-40 Hydrogenated Castor Oil (Eumulgin ® HRE 40) | | 7.5 | | | | |
| Mineral Oil | | | | | | 55.0 |
| (Propylheptyl Caprylate) Cetiol ® Sensoft | | | | | | 29.0 |
| Ester mixture of example 1 | 1.0 | 2.0 | 1.0 | 0.5 | 0.5 | 5.0 |
| Lauryl Alcohol | | | 0.5 | 0.5 | 0.5 | |
| Sodium Chloride | | | adjust viscosity | | | |
| Ethanol | | 25.0 | | | | |
| Water, Perfume, Preservatives | q.s. | q.s. | q.s. | q.s. | q.s. | q.s. |
| pH (adjusted with NaOH or citric acid) | 5.5 | 6.0 | 5.5 | 5.7 | 5.4 | 5.5 |

TABLE 18

Rinse-Off Concepts

| Ingredients (INCI) | 7 | 8 | 9 | 10 | 11 | 12 |
|---|---|---|---|---|---|---|
| MIPA-Laureth Sulfate, Laureth-4, Propylene Glycol (Texapon ® W 90) | 40.7 | 28.3 | 28.3 | 28.3 | 28.3 | |
| Sodium Laureth Sulfate (Texapon ® N 70) | | | | | | 10.9 |
| Coco-Glucoside (Plantacare ® 818 UP) | | | | | | 6.9 |
| Laureth-7 Citrate (Plantapon ® LC 7) | 5.0 | 28.3 | 28.3 | 28.3 | 28.3 | |
| Laureth-2 (Mergital ® LM2 DEO) | 10.0 | | | | | |
| PEG-7 Glyceryl Cocoate (Cetiol ® HE) | 1.1 | | | | | |
| *Soja* Oil | | | 20.7 | | | |
| Almond Oil | | | | | | 0.5 |
| Paraffinum Liquidum | | | | | 7.0 | 23.0 |
| Cyclomethicone ((Dow Corning ® 245)) | | | | | | |
| Dimethicone Copolyol (Dow Corning ® 193) | | | | 1.0 | | |
| Olus (Cegesoft ® PS6) | 22.0 | | | | | 10.0 |
| Ester mixture of example 1 | 20.0 | 41.4 | 20.7 | 40.4 | 34.4 | 15.0 |
| Acrylates Copolymer (Carbopol ® Aqua) | | | | | | 4.0 |
| Acrylates/C10-30 Alkyl Acrylate Crosspolymer (Pemulen ® TR-1) | | | | | | 0.5 |
| AMP ® 95 | 1.2 | | | | | |
| Poloxamer ® 101 | | 2.0 | 2.0 | 2.0 | 2.0 | |
| Water | | | | | | q.s. |

By exchanging the ester mixture of example 1 by the ester mixtures of examples 2, 3 or 4, the respective corresponding compositions were obtained.

Appendix—Ingredients

AMP-95, INCI: Aminomethyl Propanol, Dow Chemical Co; Abil® EM 90; INCI: Cetyl Dimethicone Copolyol; Tego Cosmetics (Goldschmidt); Allianz® OPT; INCI: Acrylates/C12-22 Alkyl Methacrylate Copolymer; Rohm and Haas; Amphisol® K; INCI: Potassium Cetyl Phosphate; Hoffmann La Roche; Admul® WOL 1403, INCI: Polyricinoleate of polyglycerol, Quest; Antaron® V 220; INCI: PVP/Eicosene Copolymer; GAF General Aniline Firm Corp. (IPS-Global); Antaron® V 216; INCI: PVP/Hexadecene Copolymer: GAF General Aniline Firm Corp. (IPS-Global); Arlacel® 83; INCI: Sorbitan Sesquioleate, Uniqema (ICI Surfacants); Arlacel® P 135, INCI: PEG-30 Dipolyhydroxystearate, Uniqema (ICI Surfactants); Bentone® 38, INCI: Quaternium-18 Hectorite, Rheox (Elementis Specialties); Carbopol® 980, INCI: Carbomer, Goodrich; Carbopol® 2984, INCI: Carbomer, Noveon, Inc.; Carbopol® ETD 2001, INCI: Carbomer, Noveon, Inc.; Carbopol® Ultrez 10, INCI: Carbomer; Noveon, Inc.; Cegesoft® C 17, Myristyl Lactate, Cognis GmbH; Cegesoft® PFO, INCI: Passiflora Incamata (EU); Cognis GmbH; Cegesoft® PS 6, INCI: Olus, Cognis GmbH, Cegesoft® SH, INCI: Shorea Stenoptera Seed Butter Cognis GmbH; Ceraphyl® 45, INCI: Diethylhexyl Malate, International Specialty Products; Cetiol® 868, INCI: Ethylhexyl Stearate, Hersteller: Cognis GmbH; Cetiol® A, INCI: Hexyl Laurate, Cognis GmbH; Cetiol® B, INCI: Dibutyl Adipate, Cognis GmbH; Cetiol® CC, INCI: Dicaprylyl Carbonate; Cognis GmbH; Cetiol® J 600, INCI: Oleyl Erucate, Cognis GmbH; Cetiol® LC, INCI: Coco-Caprylate/Caprate, Cognis GmbH; Cetiol® MM, INCI: Myristyl Myristate, Cognis GmbH; Cetiol® OE, INCI: Dicaprylyl Ether, Cognis GmbH, Cetiol® PGL, INCI: Hexyldecanol, Hexyldecyl Laurate, Cognis GmbH; Cetiol® S, INCI: Diethylhexylcyclohexane, Cognis GmbH; Cetiol® SB 45, INCI: Shea Butter Butyrospermum Parkii (Linne), Cognis GmbH; Cetiol® SN, INCI: Cetearyl Isononanoate, Cognis GmbH, Copherol® F 1300 C, INCI: Tocopherol, Cognis GmbH; Copherol 1250 C, INCI: Tocopheryl Acetate, Cognis GmbH; Cosmedia® DC, INCI: Hydrogenated Dimer Dilinoleyl/Dimethylcarbonate Copolymer; Cognis GmbH; Cosmedia® SP, INCI: Sodium Polyacrylate; Cognis GmbH; Cutina® E 24, INCI: PEG-20 Glyceryl Stearate; Cognis GmbH; Cutina® HR, INCI: Hydrogenated Castor Oil, Cognis GmbH; Cutina® MD, INCI: Glyceryl Stearate, Cognis GmbH; Cutina® PES, INCI: Pentaerythrityl Distearate, Cognis GmbH; Cutina® FS-45, INCI: Palmitic Acid, Stearic Acid, Cognis GmbH; Cutina® GMS-SE, INCI Glyceryl Stearate SE, Cognis GmbH; Cutina® LM conc, INCI: Polyglyceryl-2 Dipolyhydroxystearate, Octyldodecanol, *Copernicia Cerifera* (Carnauba) Wax, *Euphorbia Cerifera* (Candelilla) Wax, Beeswax, Cetearyl Glucoside, Cetearyl Alcohol, Cognis GmbH; Dehymuls® FCE, INCI: Dicocoyl Pentaerythrityl Distearyl Citrate, Cognis GmbH; Dehymuls® HRE 7, INCI: PEG-7 Hydrogenated Castor Oil, Cognis GmbH; Dehymuls® PGPH, INCI: Polyglyceryl-2 Dipolyhydroxystearate, Cognis GmbH; Crodesta® F-50, INCI Sucrosedistearate, Croda; Dehymuls® LE, INCI: PEG-30 Dipolyhydroxystearate, Cognis GmbH; Dow Corning® 244 Fluid, INCI: Cyclomethicone, Dow Corning; Dow Corning® 246 Fluid, Cyclopentasiloxane, Dow Corning; Dow Corning® 2502, INCI: Cetyl Dimethicone, Dow Corning; Dow Corning DC® 245 INCI: Cyclopentasiloxane, Dow Corning, Dehyquart® C 4046, INCI: Cetearyl Alcohol, Dipalmitoylethyl Hydroxyeethylmonium Methosulfate, Ceteareth-20, Cognis GmbH; Dry® Flo Plus, INCI: Aluminium Starch Octenylsuccinate, National Starch; Dry® Flo PC, INCI: Aluminum Starch Octenylsuccinate, Akzo Nobel; Elfacos® ST 37, INCI: PEG-22 Dodecyl Glycol Copolymer, Akzo-Nobel; Elfacos® ST 9, INCI: PEG-45 Dodecyl Glycol Copolymer, Akzo-Nobel; Emery® 1780, INCI: Lanolin Alcohol, Cognis Corp.; Emulgade® CM, INCI: Cetearyl Isononanoate and Ceteareth-20 and Cetearyl Alcohol and Glyceryl Stearate and Glycerin and Ceteareth-12 and Cetyl Palmitate, Cognis GmbH; Emulgade® PL 68/50, INCI: Cetearyl Glucoside, Cetearyl Alcohol, Cognis GmbH; Emulgade® SE-PF, INCI: Glyceryl Stearate (and) Ceteareth-20 (and) Ceteareth-12 (and) Cetearyl Alcohol (and) Cetyl Palmitate; Cognis GmbH, Emulgade® SUCRO, INCI: Sucrose Polystearate (and) Hydrogenated Polyisobutene, Cognis GmbH; Eumulgin® B1, INCI: Ceteareth-12, Cognis GmbH, Eumulgin® B 2, INCI: Ceteareth-20, Cognis GmbH; Eumulgin® HRE 40, INCI: PEG-40 Hydrogenated Castor Oil, Cognis GmbH; Eumulgin® Prisma INCI: Disodium Cetearyl Sulfosuccinate; Eumulgin® SG, INCI: Sodium Stearoyl Glutamate, Cognis GmbH; Eumulgin® VL 75, INCI: Lauryl Glucoside (and) Polyglyceryl-2 Dipolyhydroxystearate (and) Glycerin; Cognis GmbH; Eusolex® OCR, INCI: Octocrylene, Merck; Eusolex® T 2000, INCI: Titanium Dioxide, Alumina, Simethicone, Merck; Eusolex® AQUA, INCI: Water and Titanium Dioxide and Alumina and Sodium Metaphosphate and Phenoxyethanol and Sodium Methylparaben, Merck; Eutanol® G, INCI: Octyldodecanol, Cognis GmbH; Eutanol® G 16, INCI: Hexyldecanol, Cognis GmbH; Eutanol® G 16 S, INCI: Hexyldecyl Stearate, Cognis GmbH; Finsolv® TN, INCI: C 12/15 Alkyl Benzoate, Findex (Nordmann/Rassmann); Fitoderm®, INCI Squalane, Cognis GmbH; Generol® R, INCI: *Brassica Campestris* (Rapseed) Sterols, Cognis GmbH; Glucate® DO, INCI: Methyl Glucose Dioleate, NRC Nordmann/Rassmann; Hispagel® 200, INCI: Glycerin, Glyceryl Polyacrylate, Cognis GmbH; Hostaphat® KL 340 N, INCI: Trilaureth-4 Phosphate, Clariant; Hydagen® C.A.T., INCI Triethyl Citrate, Cognis GmbH; Hydagen® DCMF, INCI: Chitosan, Cognis GmbH; Insect Repellent® 3535, INCI: Ethyl Butylacetylaminopropionate, EMD Chemicals Inc; Isolan® PDI, INCI: Diisostearoyl Polyglyceryl-3 Diisostearate, Goldschmidt AG; Isolan® GPS, INCI: Polyglyceryl-4 Diisostearate/Polyhydroxystearate/Sebacate, Evonik Goldschmidt; Isolan® GI 34, INCI: Polyglyceryl-4 Isostearate, Evonik Goldschmidt; Irwinol® LS 9319, INCI: Octyldecanol, Irvingia Gabonensis Kernel Butter, Hydrogenated Coco-Glycerides, Keltrol®, INCI: Xanthan Gum, CP Kelco; Lameform® TGI, INCI: Polyglyceryl-3 Diisostearate, Cognis GmbH; Lanette® 14, INCI: Myristyl Alcohol, Cognis GmbH; Lanette® 18, INCI: Stearyl Alcohol, Cognis GmbH; Lanette® 22, INCI: Behenyl Alcohol, Cognis GmbH; Lanette® E, INCI: Sodium Cetearyl Sulfate, Cognis GmbH; Lanette® O, INCI: Cetearyl Alcohol, Cognis GmbH; Locron® L, INCI: Aluminium Chlorhydrate, Clariant; Lucentite® SAN, INCI: Quaternium-18 Hectorit, Co-Op Chemical Co., Ltd.; Microna® Matte White ((INCI: Titanium Dioxide, Zinc Oxide); Microna® Matte Black (INCI: Iron Oxide; Mica); Microna® Matte Yellow (INCI: Iron Oxide; Mica); Microna® Matte Red (INCI: Iron Oxide; Mica), Cosmetic white C47056 (INCI: Titanium Dioxide, Mica); FDC Yellow 6 Al Lake C705270 (INCI: Colour Index 15985); DC Red 7 Ca Lake C 19003 (INCI: Colour Index 15850); Irodin 100 Silverpearl, (INCI: Mica, Titanium dioxide); Colophane Claire type Y (INCI: Colophonium); Monomuls® 90-O 18, INCI: Glyceryl Oleate, Cognis GmbH; Monomuls® 90 L 12, INCI: Glyceryl Laurate, Cognis GmbH; Myrj® 51, INCI: PEG-30-Sterate, Uniqema; Myritol® 312, INCI: Caprylic/Capric Triglyceride, Cognis GmbH; Myritol® 331, INCI: Cocoglycerides, Cognis GmbH; Myritol® PC, INCI: Propylene Glycol Dicaprylate/Dicaprate, Cognis GmbH; Neo Heliopan® 303, INCI: Octocrylene, Symrise; Neo Heliopan® AP, INCI: Disodium Phenyl Dibenzimidazole Tetrasulfonate, Symrise; Neo Heliopa® AV, INCI: Ethylhexyl Methoxycinnamate, Symrise; Neo Heliopan® BB, INCI: Benzophenone-3, Symrise; Neo Heliopan® E 1000, INCI: Isoamyl-p-Methoxycinnamate, Symrise; Neo Heliopan® Hydro, INCI: Phenylbenzimidazole Sulfonic Acid, Symrise; Neo Heliopan® MBC, INCI: 4-Methylbenzylidene Camphor, Symrise; Neo Heliopan® OS, INCI: Ethylhexyl Salicylate, Symrise; Novata® AB, INCI: Cocoglycerides, Cognis GmbH; Parsol® 1789, INCI: Butyl Methoxydibenzoylmethane, Hoffmann-La Roche (Givaudan); Pemulen® TR-2 Polymer, INCI: Acrylates/C10-30 Alkylacrylate Crosspolymer, Noveon, Inc.; Photonyl® LS, INCI: Arginine, Disodium Adenosine Triphosphate, Mannitol, Pyridoxine HCL, Phenylalanine, Tyrosine, Laboratoires Serobiologiques (Cognis); Prisorine® 3505, INCI: Isostearic Acid; Uniqema; Prisorine® 3758, INCI: Hydrogenated Polyisobutene, Uniqema; Rezal 36G, INCI: Aluminum Zirconium Tetrachlorohydrex GLY, Reheis, Inc; Rheocare® C Plus, INCI Carbomer, Cognis GmbH; Ronasphere® LDP (INCI: Silica, Titanium dioxide, Iron Oxides); Squatol® S, INCI: Hydrogenated Polyisobutene, BASF Corp.; Poloxamer® 101, INCI: Poloxamer, BASF SE; SFE® 839, INCI: Cyclopentasiloxane and Dimethicone/Vinyl Dimethicone Crosspolymer, GE Silicones; Silikonöl Wacker AK® 350, INCI: Dimethicone, Wacker; Tego® Care 450, INCI: Polyglyceryl-3 Methylglucose Distearate, Goldschmidt; Tego® Care CG 90, INCI: Cetearyl Glucoside, Goldschmidt; Tegosoft® DEC, INCI: Diethylhexyl Carbonate, Goldschmidt; Tinosorb® S, INCI: Bis-Ethylhexyloxyphenol Methoxyphenyl Triazine; Ciba Specialty Chemicals Corporation; Tinosorb® M, INCI: Methylene Bis-Benzotriazolyl Tetramethylbutylphenol, Ciba Specialty Chemicals Corporation; Tween® 60, INCI: Polysorbate 60, Uniqema (ICI Surfactants), Uvasorb® HEB, INCI: Diethylhexyl Butamido Triazone, 3V Inc.; Unirep® U-18, INCI: Dimethyl Phthalate and Diethyl Toluamide and Ethyl Hexanediol, Induchem AG; Uvinul® T 150, INCI: Ethylhexyl Triazone, BASF; Uvinul® A plus, INCI: Diethylamino Hydroxybenzoyl Hexyl Benzoate, BASF; Veegum® Ultra, INCI: Magnesium Aluminium Silicate, R. T. Vanderbilt Company, Inc; Veegum® Plus, INCI: Magnesium Aluminum Silicate and Cellulose Gum, R. T. Vanderbilt Company, Inc; Z-Cote® HP 1, INCI: Zinc Oxide and Triethoxy-caprylylsilane, BASF, Zinc Oxide NDM, INCI: Zinc Oxide, Symrise.

The invention claimed is:

1. A mixture of esters according to the general formula (I), $$R_1-C(=O)-O-R_2$$

wherein $R_1$ is an alkyl moiety with 7 to 9 carbon atoms and $R_2$ is a linear alkyl moiety with 8 to 10 carbon atoms,
the mixture comprising 20 to 40 weight % or 40 to 60 weight % of ester of the general formula (I) wherein $R_1$ is an alkyl moiety with 9 carbon atoms, based on a total amount of esters according to formula (I) in the mixture and wherein the mixture comprises 20 to 40 weight % or 40 to 60 weight % of ester of the general formula (I) wherein $R_2$ is a linear alkyl moiety with 10 carbon atoms, based on a total amount of esters according to formula (I) in the mixture.

2. The mixture of esters according to claim 1, wherein the mixture comprises 20 to 40 weight % of an ester of the general formula (I) wherein $R_2$ is a linear alkyl moiety with 10 carbon atoms, based on the total amount of esters according to formula (I) in the mixture.

3. The mixture of esters according to claim 1, wherein $R_1$ is a linear alkyl moiety.

4. The mixture of esters according to claim 1, wherein $R_1$ is a branched alkyl moiety.

5. A process for the production of ester mixtures of formula (I), $R_1-C(=O)-O-R_2$ comprising reacting a carbon acid or a mixture of carbon acids $R_1$—COOH with an alcohol or a mixture of alcohols $R_2$—OH, wherein $R_1$ is an alkyl moiety with 7 to 9 carbon atoms and $R_2$ is a linear alkyl moiety with 8 to 10 carbon atoms, in such a ratio that the resulting ester mixture comprises 20 to 40 weight % or 40 to 60 weight % of ester of the general formula (I) wherein $R_1$ is an alkyl moiety with 9 carbon atoms, based on a total amount of esters according to formula (I) in the ester mixture and the mixture comprises 20 to 40 weight % or 40 to 60 weight % of an ester of the general formula (I) wherein $R_2$ is a linear alkyl moiety with 10 carbon atoms, based on the total amount of esters according to formula (I) in the mixture.

6. A process for the production of ester mixtures of formula (I), $R_1-C(=O)-O-R_2$ wherein a carbon acid alkyl ester or a mixture of carbon acid alkyl esters $R_1-C(=O)-R_3$ is reacted with an alcohol or a mixture of alcohols $R_2$—OH, wherein $R_1$ is an alkyl moiety with 7 to 9 carbon atoms, $R_2$ is a linear alkyl moiety with 8 to 10 carbon atoms and $R_3$ is an alkyl moiety with 1, 2, 3, or 4 carbon atoms, in the presence of a transesterification catalyst in such a ratio that the resulting ester mixture comprises 20 to 40 weight % or 40 to 60 weight % of an ester of the general formula (I) wherein $R_1$ is an alkyl moiety with 9 carbon atoms, based on a total amount of esters according to formula (I) in the ester mixture and the mixture comprises 20 to 40 weight % or 40 to 60 weight-% of an ester of the general formula (I) wherein $R_2$ is a linear alkyl moiety with 10 carbon atoms, based on a total amount of esters according to formula (I) in the mixture.

7. A cosmetic and/or pharmaceutical composition comprising 0.1 to 95 weight % of a mixture of esters according to the general formula (I), $$R_1-C(=O)-O-R_2$$

wherein $R_1$ is an alkyl moiety with 7 to 9 carbon atoms and wherein $R_2$ is a linear alkyl moiety with 8 to 10 carbon atoms,
wherein the mixture comprises 20 to 40 weight % or 40 to 60 weight % of ester of the general formula (I)—wherein R1 is an alkyl moiety with 9 carbon atoms, based on a total amount of esters according to formula (I) in the mixture
and wherein the mixture comprises 20 to 40 weight % or 40 to 60 weight % of ester of the general formula (I) wherein $R_2$ is an alkyl moiety with 10 carbon atoms, based on a total amount of esters according to formula (I) in the mixture.

8. A method of preparing cosmetic and/or pharmaceutical compositions comprising adding the mixture of esters according to claim 1 to the cosmetic and/or pharmaceutical compositions.

9. The method according to claim 8 wherein the mixture is added as an oil component and/or solubiliser.

10. The mixture of esters according to claim 1, wherein $R_1$ is a saturated alkyl moiety.

11. The mixture of esters according to claim 10, wherein $R_1$ is n-heptyl, n-octyl or n-nonyl.

12. The mixture of esters according to claim 1, wherein $R_2$ is a saturated alkyl moiety.

13. The mixture of esters according to claim 4, wherein an amount of branched esters is 50 or less than 50 weight %, based on the total amount of esters according to formula (I) in the mixture.

14. The mixture of esters according to claim 1 which is liquid at 20° C.

15. The process of claim 5, wherein the carbon acid or carbon acid mixture is reacted with the alcohol or alcohol mixture in the presence of an acid or base esterification catalyst, or an enzyme catalyst.

16. The process of claim 15, wherein the esterification catalyst is a tin catalyst.

17. The process of claim 5, wherein the process is substantially water-free.

18. The process of claim 6, wherein $R_3$ is methyl, ethyl or n-butyl.

19. The process of claim 18 which is substantially water-free and is carried out in the presence of a sodium methylate or tetra-alkyl titanate transesterification catalyst.

* * * * *